(12) United States Patent
Yang et al.

(10) Patent No.: US 7,705,040 B2
(45) Date of Patent: Apr. 27, 2010

(54) REAGENTS FOR HIGHLY SPECIFIC DETECTION OF PEROXYNITRITE

(75) Inventors: Dan Yang, Hong Kong (CN); Hua-Li Wang, Hong Kong (CN); Zhen-Ning Sun, Hong Kong (CN); Jian-Gang Shen, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 1156 days.

(21) Appl. No.: 11/245,529

(22) Filed: Oct. 7, 2005

(65) Prior Publication Data

US 2007/0082403 A1 Apr. 12, 2007

(51) Int. Cl.
*A61K 31/55* (2006.01)
*C07D 309/00* (2006.01)

(52) U.S. Cl. .................................. 514/455; 549/359
(58) Field of Classification Search ................ 549/359; 436/106; 514/455
See application file for complete search history.

(56) References Cited

FOREIGN PATENT DOCUMENTS

WO 0164664 7/2001
WO 2004040296 5/2004

OTHER PUBLICATIONS

Yang et al., Journal of Organic Chemistry, 2000, 65:4179-4184.*
Augusto O. et al., "Detection of Secondary Radicals from Peroxynitrite Mediated Oxidations by Electron Spin Resonance," Methods in Enzymology, 1996, 269:346-354.
Beal M. "Oxidatively Modified Proteins in Aging and Disease," Free Radical Biol. & Medicine, 2002, 32(9):797-803.
Beckman, J.S. et al. "Nitric Oxide, Superoxide, and Peroxynitrite: The Good, The Bad, and The Ugly," Am. J. Physiol. 271 (Cell Physiol. 40), 1996, C1424-C1437.
Beckman, J.S. et al. "Kinetics of Superoxide Dismutase-and Iron-Catalyzed Nitration of Phenolics by Peroxynitrite," Archives of Biochemistry and Biophysics, 1992, 298(2):438-445.
Crow, J.P. "Dichlorodihydrofluorescein and Dihydrorhodamine 123 are Sensitive Indicators of Peroxynitrite in Vitro: Implications for Intracellular Measurement of Reactive Nitrogen and Oxygen Species," Nitric Oxide: Biology and Chemistry, 1997, 1(2):145-157.
Cuzzocrea, S. et al. "Antioxidant Therapy: A New Pharmacological Approach in Shock, Inflammation, and Ischemia/Reperfusion Injury," Pharmacol. Rev., 2001, 53:135-159.
Feelisch, M. "Biotransformation to Nitric Oxide of Organic Nitrates in Comparison to Other Nitrovasodilators," Eur. Heart J., 1993, 123-132.
Gatti, R.M. "Formation of Spin Trap Adducts During the Decomposition of Peroxynitrite," Archives of Biochemistry and Biophysics, 1998, 349(1):36-46.
Gatti, R.M. "Peroxynitrite-Mediated Oxidation of Albumin to the Protein-Thiyl Free Radical," FEBS Letters, 1994, 287-290.
Groves, J.T. "Peroxynitrite: Reactive, Invasive and Enigmatic," Curr. Opinion in Chem. Biology, 1999, 3:226-235.
Gryglewski, R.J. "Superoxide Anion is Involved in the Breakdown of Endothelium-Derived Vascular Relaxing Factor," Nature, 1986, 320:454-456.
Hughes, M.N., "The Chemistry of Pernitrites, Part 1. Kinetics of Decomposition of Pernitrous Acid," J. Chem. Soc., 1968, 450-452.
Ischiropoulos, H. "Biological Tyrosine Nitration: A Pathophysiological Function of Nitric Oxide and Reactive Oxygen Species," Archives of Biochemistry and Biophysics, 1998, 356(1):1-11.
Ischiropoulos, H. Detection of Reactive Nitrogen Species Using 2, 7-Dichlorodihydrofluorescein and Dihydrorhodamime 123, "Methods in Enzymology," 1999 301:367-373.
Corrie, J.E.T., "Synthesis of Photoactivatable Fluorescein Derivatives Bearing Side Chains with Varying Properties," J. Chem. Soc. Perkin Trans. 1995, 1993-2000.
Kaur, H., "Evidence for Nitric Oxide-Mediated Oxidative Damage in Chronic Inflammation," FEBS Letters, 1994, 350:9-12.
Keith, W.G. "Kinetics of Decomposition of Peroxynitrous Acid," J. Chem. Soc. (A), 1969, 90.
Kooy, N. et al. "Oxidation of 2', 7'-Dichlorofluorescin by Peroxynitrite," Free Rad. Res., 1997, 27(3), 245-254.
Koppenol, W. "100 Years of Peroxynitrite Chemistry and 11 Years of Peroxynitrite Biochemistry," Redox Report, 2001, 6(6):339-341.
Lipton, S.A. "A Redox-Based Mechanism for the Neuroprotective and Neurodestructive Effects of Nitric Oxide and Related Nitroso-Compounds," Nature, 1993, 364:626-632.
McWatt, M. "Parallel Combinatorial Synthesis of Glycodendrimers and Their Hydrogelation Properties," Eur. J. Org. Chem., 2001, 2535-2545.
MacMillan-Crow, L.A., "Nitration and Inactivation of Manganese Superoxide Dismutase in Chronic Rejection of Human Renal Allografts," Proc. Natl. Acad. Sci. USA, 1996, 93:11853-11858.
Miles, A.M. et al. "Modulation of Superoxide-Dependent Oxidation and Hydroxylation Reactions by Nitric Oxide," J. Biol. Chem., 1996, 271(1):40-47.
Gabe, Y. et al. "Highly Sensitive Fluorescence Probes for Nitric Oxide Based on Boron Dipyrromethene Chromophore-Rational Design of Potentially Useful Bioimaging Fluorescence Probe," J. Am. Chem. Soc., 2004, 126:3357-3367.
Pappolla, M.A "An Assessment of the Antioxidant and the Antimyloidogenic Properties of Melatonin: Implications for Alzheimer's Disease," J. Neural Transmission, 2000, 107:203-231.
Radi, R. "Peroxynitrite Reactions and Diffusion in Biology," Chem. Res. Toxicol, 1998, 11:720-721.
Radi, R. et al. "Peroxynitrite-Induced Membrane Lipid Peroxidation: The Cytotoxic Potential of Superoxide and Nitric Oxide," Archives of Biochemistry and Biophysics, 1991, 288(2):481-487.
Radi R. et al. "Peroxynitrite Oxidation of Sulfhydryls," J. Biol. Chem., 1991, 266(7):4244-4250.
Radi R. "Unraveling Peroxynitrite Formation in Biological Systems," Free Radical Biology & Medicine, 2001, 30(5):463-488.

(Continued)

*Primary Examiner*—Rei-tsang Shiao
(74) *Attorney, Agent, or Firm*—Jones Day

(57) ABSTRACT

This invention provides compositions which specifically reacts with peroxynitrite rather than other reactive oxygen species and reactive nitrogen species. This invention also provides related agents for measuring peroxynitrite. This invention also provides related methods for measuring peroxynitrite in a sample, high-throughput screening fluorescent methods for detecting peroxynitrite and high-throughput methods for screening compounds that increase or decrease the production of peroxynitrite comprising using such compositions and agents.

61 Claims, 24 Drawing Sheets

OTHER PUBLICATIONS

Rodenas J. "Different Roles for Nitrogen Monoxide and Peroxynitrite in Lipid Peroxidation Induced by Activated Neutrophils," Free Radical Biology & Medicine, 2000, 28(3):374-380.

Romero N. et al. "Diffusion of Peroxynitrite in the Presence of Carbon Dioxide," Archives of Biochemistry and Biophysics, 1999, 368(1):23-30.

Royall, J.A. "Evaluation of 2', 7'-Dichlorofluorescin and Dihydrorhodamine 123 as Fluorescent Probes for Intracellular H2O2 in Cultured Endothelial Cells," Archives of Biochemistry and Biophysics, 1993, 302(2):348-355.

Rychnovsky, S.C. "Stereochemistry of the Macrolactins," J. Am. Chem. Soc., 1992, 114:671-677.

Setsukinai, K. et al. "Development of Novel Fluorescence Probes that Can Reliably Detect Reactive Oxygen Species and Distinguish Specific Species," J. Biol. Chem., 2003, 278(5):3170-3175.

Shi, H. et al., "Formation of Phospholipid Hydroperoxides and Its Inhibition by α-Tocopherol in Rat Brain Synaptosomes Induced by Peroxynitrite," Biochem. Biophys. 1999, 257:651-656.

Squadrito, G.L. "Oxidative Chemistry of Nitric Oxide: The Roles of Superoxide, Peroxynitrite, and Carbon Dioxide," Free Radical Biology & Medicine, 1998, 25(4/5):392-403.

Szabo C. "Multiple Pathways of Peroxynitrite Cytotoxicity," Toxicology Letters, 2003, 105-112.

Tarpey, M. M. "Methods of Detection of Vascular Reactive Species," Circ. Res. 2001, 89:224-236.

White, C.R. "Superoxide and Peroxynitrite in Atherosclerosis," Proc. Natl. Acad. Sci. USA, 1994 91:1044-1048.

Yang D. et al. "Regioselective Intramolecular Oxidation of Phenols and Anisoles by Dioxiranes Generated in Situ," J. Org. Chem., 2000(65):4179-4184.

* cited by examiner ss-3

Emission Spectrum of ss-6 (20μM,1% CH$_3$CN)
in 0.1M sodium phosphate buffer (pH 7.4)

Emission Spectrum of ss-6 (20 μM,1% $CH_3CN$) in 0.1M sodium phosphate buffer (pH 7.4) 0.5h after the reaction of 15 equiv of $ONOO^-$ An absorption spectrum of 20 μM ss-6

Emission Spectra of ss-6 (20μM, 1% $CH_3CN$) in 0.1M sodium phosphate buffer (pH 7.4) 0.5h after the reaction of various amount of ONOO⁻ ranging from 0 to 300μM ss-6 (20μM,1% CH$_3$CN) in 0.1M sodium phosphate buffer(pH 7.4)

ss-7 ss-8 ss-9 ss-10 ss-11 ss-12

Emission Spectrum of ss-12 (20μM,1% CH3CN)
in 0.1M sodium phosphate buffer (pH 7.4)

Emission Spectrum of ss-12 (20 μM, 1% $CH_3CN$) in 0.1M sodium phosphate buffer (pH 7.4) 0.5h after the reaction of 15 equiv of $ONOO^-$ An absorption spectrum of 20 μM ss-12

Emission Spectra of ss-12 (20μM,1% CH$_3$CN) in 0.1M sodium phosphate buffer (pH 7.4) 0.5h after the reaction of various amount of ONOO⁻ ranging from 0 to 300μM ss-12 (20μM,1% CH$_3$CN) in 0.1M sodium phosphate buffer(pH 7.4)

US 7,705,040 B2

REAGENTS FOR HIGHLY SPECIFIC DETECTION OF PEROXYNITRITE

Throughout this application, various references are cited. Disclosure of these references in their entirety is hereby incorporated by reference into this application to more fully describe the state of the art to which this invention pertains.

TECHNICAL FIELD OF THE INVENTION

This invention relates generally to the field of detecting and measuring peroxynitrite. More specifically, the invention relates to compounds useful as agents to specifically detect and measure peroxynitrite. The invention includes probe molecules, methods for their preparation and use as agents to detect and measure peroxynitrate in living cells and living tissues.

BACKGROUND OF THE INVENTION

Peroxynitrite ($ONOO^-$), an isomer of nitrate, has been known for about one century. During the past decade it has been extensively studied due to its potential important role in biology and medicine (Gryglewski, R., *Nature* 1986, 320, 454; Beckman, J. S., *Am. J. Physiol. Cell Physiol.* 1996, 271, C1424; Squadrito, G. L. et al., *Free Radical Biol. & Med.* 1998, 25, 797; Groves, J. T., *Curr. Opin. Chem. Biol.* 1999, 3, 226; Radi, R. et al., *Free Radical Biol. & Med.* 2001, 30, 463-488; Tarpey, M. M. et al., *Circ. Res.* 2001, 89, 224-236; and Koppenol, W. H., *Redox Report* 2001, 6, 339-341). Peroxynitrite can be formed in vivo from the diffusion-controlled reaction (k =0.4–1.9×$10^{10}$ $M^{-1}s^{-1}$) of nitric oxide (NO) and superoxide ($O_2^-$) in one to one stoichiometry (Hughes, M. N. et al., *J. Chem. Soc. (A)* 1968, 450) and the concentration of NO is the key controller during the peroxynitrite production process. The reaction between nitric oxide and superoxide proceeds when the concentration of NO increases and can overcome dismutation by superoxide dismutase. This situation occurs when nitric oxide (NO) is overproduced by cytokine-stimulated inducible NO synthase (iNOS). The pathological activity of $ONOO^-$ is related to its reaction with the biologically ubiquitous $CO_2$, thereby producing the highly reactive radicals $CO_3.$ and $NO_2.$ in about 35% yield (Radi, R. et al., *Free Radical Biol. & Med.* 2001, 30, 463-488). As a result, peroxynitrite can nitrate tyrosine (Ischiropoulos, H., *Arch. Biochem. Biophys.* 1998, 356, 1-11, and Beckman J. S. et al., *Arch Biochem Biophys,* 1992, 298, 438-445) and oxidize proteins, lipids (Radi, R. et al., *Arch. Biochem. Biophys.* 1991, 288, 481, and Shi, H. et al., *Biochem. Biophys. Res. Commun.* 1999, 257, 651) and iron and sulfur clusters of biological molecules (Radi R, et al., *J. Biol. Chem,* 1991, 266, 4244-4250). Like other oxidizing agents in living organisms, peroxynitrite and its protonated form have been associated with both beneficial and harmful effects. Macrophages produce peroxynitrite as a host-defense response to bacterial invasion. However, several studies have implicated that peroxynitrite contributes to tissue injury in a number of human diseases such as ischemic reperfusion injury, rheumatoid arthritis, septic shock, multiple sclerosis, atherosclerosis, stroke, inflammatory bowl disease, cancer, and several neurodegenerative diseases (MacMillan-Crow, L. A. et al., *Proc. Natl. Acad. Sci. USA* 1996, 93, 11853; Rodenas, J. et al., *Free Radical. Biol. & Med.* 2000, 28, 374; Cuzzocrea, S. et al., *Pharmacol Rev.* 2001, 53, 135; Szabo, C. *Toxicol. Lett.* 2003, 140, 105; White, C. R. et al., *Proc. Natl. Acad. Sci. USA* 1994, 91, 1044; Lipton, S. A. et al., *Nature* 1993, 364, 626; Pappolla, M. A. et al., *J. Neural Transm.* 2000, 107, 203; and Beal, M. F., *Free Radical Biol. & Med* 2002, 32, 392).

Explanation of the critical role of peroxynitrite in living organisms has become increasingly important. Although it is stable in alkaline solution, peroxynitrite decays rapidly upon protonation at physiological pH. The short half-life of peroxynitrite in biological system (1 s in buffers of neutral pH values and less than 100 ms in cells) precludes its direct isolation (Denicola, A. et al. *Arch. Biochem. Biophys.* 1996, 333, 49-58). Even though solid evidence is known regarding the formation of peroxynitrite in vivo, tools for unambiguous detection and quantitation of peroxynitrite in cells and tissues are not yet available.

Up to now, the available analytical methods for detecting and measuring peroxynitrite can be classified into three types. The first type is the electrochemical sensor, which is used to estimate the amounts of peroxynitrite generated in cells under oxidative stress. (Augusto, O. et al., *J. Methods Enzymol.* 1996, 269, 346-354; Gatti, R. M. et al., *FEBS Lett,* 1994, 348, 287-290; Gatti, R. M. et al. *Arch. Biochem. Biophys.* 1998, 349, 36-46; and Karoui, H. et al., *J. Biol. Chem.* 1996, 271, 6000-6009). But this method requires manipulation of sophisticated apparatus and does not allow spatial imaging of peroxynitrite.

The second type relies on the employment of oxidation probes. For example, DCFH (2',7'-dichlordihydrofluorescein) and DHR 123 (dihydrorhodamine 123), which can be oxidized by peroxynitrite to yield highly fluorescent molecules, have been used for monitoring peroxynitrite in cells and tissues (Royall, J. A. et al., *Arch. Biochem. Biophys.* 1993, 302, 348-355; Kooy, N. W. et al., *Free Radic. Biol. Med.* 1994, 16, 149-156; Kooy, N. W. et al., *Free Radic. Biol. Res.* 1997, 27, 245-254; Crow, J. P. *Nitric Oxide.* 1997, 1, 145-157; Ischiropoulos, H et al., *Methods Enzymol.* 1999, 301, 367-373; and Miles, A. M. et al., *J. Biol. Chem.* 1996, 271, 40-47). However, the mechanism of oxidation of DCFH and DHR by peroxynitrite remains largely unknown and these probes can also be oxidized by many other ROS (reactive oxygen species) produced by cells. A similar problem can be found in luminal chemiluminescence system for detecting peroxynitrite in cell culture solution. HPF (hydroxyphenyl fluorescein) can distinguish between peroxynitrite and nitric oxide, but it gives out higher fluorescent signal with hydroxyl radical than does with peroxynitrite (Setsukinai, K. et al., *J. Biol. Chem.* 2003, 278, 3170-3175; International Publication No. WO 01/64664 (Nagano et al.); and International Publication No. WO2004040296 (Nagano et al.)).

The third type utilizes the footprinting reaction of biological molecules. For example, 3-nitrotyrosine, a nitration product generated after oxidation of tyrosine residues of proteins by peroxynitrite in biological systems, can be detected by immunochemical methods (Kaur, H.; et al., *FEBS Lett.* 1994, 350, 9-12). NADH (reduced nicotamide adenine dinucleotide) has also been used recently for monitoring of peroxynitrite concentration in buffers by fluorescence. However, at the moment, there are no entirely specific chemical modifications of either probes or biomolecules that can directly indicate the generation of peroxynitrite in cells in an unambiguous manner. It implies that other reactive oxygen species and reactive nitrogen species present in the biological systems may compete with peroxynitrite and interfere with the results.

Several methods have been known for the detection/measurement of peroxynitrite, including electrochemical method, the chemiluminescence method and the footprinting method. However, these methods require tedious and time-consuming control experiments using a combination of scavengers and inhibitors, and give low sensitivity and specificity. Thus, to facilitate the direct studies of peroxynitrite in bio-

SUMMARY OF THE INVENTION

This invention relates to novel compounds which are used for unambiguous detection and measurement of peroxynitrite. Specifically, this invention provides compounds, which specifically react with peroxynitrite rather than other reactive oxygen species and reactive nitrogen species, represented by the following general formula (I), (II), (III), or a salt thereof:

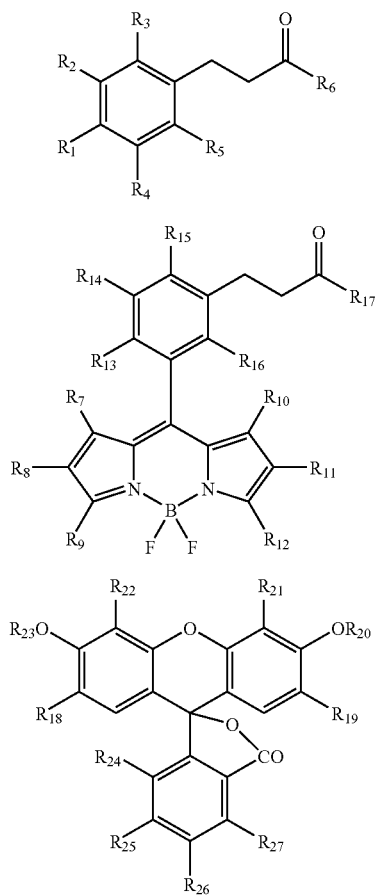

wherein $R_i$ (i=1-22) is as defined in the "Detailed Description Of The Invention" below.

This invention also provides agents for measuring peroxynitrite comprising any of the compounds mentioned above.

The invention also provides methods for measuring peroxynitrite in a sample comprising the steps:
a) contacting any of the compounds mentioned above with the sample, and
b) measuring fluorescence of a resulting compound generated by a reaction between the compound and peroxynitrite present in the sample.

The invention also provides a high-throughput screening fluorescent method for detecting peroxynitrite comprising using an agent for measuring peroxynitrite, wherein the agent comprising any of the compounds mentioned above.

The invention also provides a high-throughput method for screening compounds that increase or decrease the production of peroxynitrite comprising using any of the compounds mentioned above.

DETAILED DESCRIPTION OF THE INVENTION

Definitions

Figure 1:
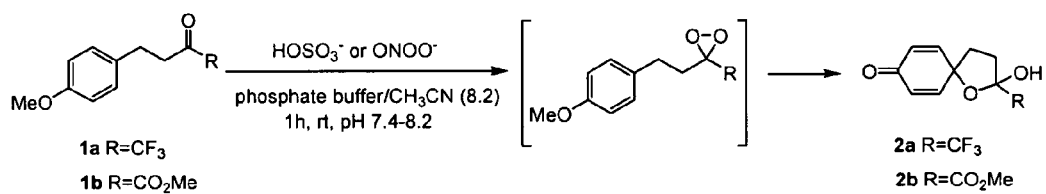
FIG. 1 illustrates the reaction of the oxidation of ketone (1a/1b) by peroxynitrite or Oxone® ($2KHSO_5 \cdot KHSO_4 \cdot K_2SO_4$).

As used in this application, except as otherwise expressly provided herein, each of the following terms shall have the meaning set forth below.

"Alkyl" refers to a fully saturated acyclic monovalent radical containing carbon and hydrogen, and which may be branched or a straight chain. Examples of alkyl groups are methyl, ethyl, n-butyl, t-butyl, n-heptyl, and isopropyl. "Lower alkyl" refers to an alkyl radical of one to six carbon atoms, as exemplified by methyl, ethyl, n-butyl, i-butyl, t-butyl, isoamyl, n-pentyl, and isopentyl.

"Alkenyl" refers to a monovalent or divalent unsaturated, preferably monounsaturated, radical containing carbon and hydrogen, and which may be cyclic, branched or a straight chain. "Lower alkenyl" refers to such a radical having one to five carbon atoms.

"Aryl" refers to a substituted or unsubstituted monovalent aromatic radical, generally having a single ring (e.g., benzene) or two condensed rings (e.g., naphthyl). Monocyclic aryl groups are generally preferred. The term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a group or groups preferably selected from fluorine, chlorine, bromine, iodine, methyl, ethyl, hydroxyl, hydroxymethyl, nitro, amino, methylamino, dimethylamino, methoxy, halomethoxy, and halomethyl.

"Aralkyl" refers to an alkyl, preferably lower alkyl, substituent which is further substituted with an aryl group; examples are benzyl and phenethyl.

"Fluorophore" refers to a small molecule, or a part of a larger molecule, that can be excited by light to emit fluorescence. Preferably, fluorophores efficiently produce fluorescence upon excitation with light which has a wavelength in the range of about 200 to about 1000 nanometers, preferably in the range of about 500 to 800 nanometers. A fluorophore is preferably selected from acridine orange, anthracene ring, allophycocyanin, BODIPY, cyanines, coumarin, Edans, Eosin, Erythrosin, fluorescamine, fluorescein, FAM (carboxyfluorescein), HEX (hexachlorofluorescein), JOE (6-carboxy-4',5'-dichloro-2',7'-dimethoxy-fluorescein), Oregon Green, phycocyanin, phycoerythrin, rhodamine, ROX (Carboxy-X-rhodamine), TAMRA (carboxytetramethyl-rhodamine), TET (tetrachloro-fluorescein), Texas red, tetramethylrhodamine, and xanthines. Such groups are reported in the *Handbook of Fluorescent Probes and Research Products*, 9th Edition, Molecular Probes, Eugene, Oreg., Haughland, 2003.

"Inorganic ester" refers to a product of the reaction of an inorganic acid and an alcohol. Inorganic esters mainly result from the condensation of an inorganic acid and an alcohol.

The term "salt" refers to which formed by standard acid-base reactions with basic groups, such as amino groups, having a counterion derived from an organic or inorganic acid. Such counterions include chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like.

The term "physiologically acceptable salt" encompasses carboxylate salts having organic and inorganic cations, such as alkali and alkaline earth metal cations (e.g., lithium, sodium, potassium, magnesium, barium and calcium); ammonium; or organic cations, for example, dibenzylammonium, benzylammonium, 2-hydroxyethylammonium, bis(2-hydroxyethyl)ammonium, phenylethylbenzylammonium, and the like. Other cations encompassed by the above term include the protonated form of procaine, quinine, and N-methylglucosamine, and the protonated forms of basic amino acids, such as glycine, ornithine, histidine, phenylalanine, lysine, and arginine.

Embodiments of the Invention

As mentioned above, this invention provides compounds which specifically react with peroxynitrite rather than other reactive oxygen species and reactive nitrogen species. The compounds have the following general formula (I):

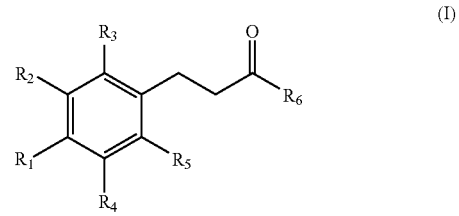

wherein:

$R^1$ is $OR'_1$, or $NR'_2R'_3$, wherein $R'_1$, $R'_2$, and $R'_3$ are independently hydrogen or a group selected from alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether;

$R_2$, $R_3$, $R_4$, and $R_5$ are independently hydrogen or a group selected from halogen, alkyl, alkoxy, alkyloxy, polyether, $R_2$ and $R_3$ come together to form a 5, 6, or 7-membered ring which is selected from aryl, heterocyclic, heteroaryl or heteroaromatic, or $R_4$ and $R_5$ come together to form a 5, 6, or 7-membered ring which is selected from aryl, heterocyclic, heteroaryl or heteroaromatic;

$R_6$ is an electron-withdrawing group selected from $CF_3$, halogen-substituted lower alkyl (e.g., $CF_nH_{3-n}$, wherein n is 1 or 2), or $(C=O)-O-W_i$, wherein $W_1$ is a group selected from alkyl, alkenyl, alkynyl, cycloalkyl, cycloalkenyl, cycloalkynyl, aryl, alkaryl, or arylalkyl; and a fluorophore or masked fluorophore may be covalently linked to one of $R_i$ (i=1-5).

In addition, the compounds discussed immediately above have the following further embodiments:

$R_2$ and $R_3$ come together to form a 5, 6, or 7-membered ring which is selected from aryl, heterocyclic, heteroaryl or heteroaromatic;

$R_4$ and $R_5$ come together to form a 5, 6, or 7-membered ring which is selected from aryl, heterocyclic, heteroaryl, or heteroaromatic;

$R'_1$ is $CH_3$ or $OCH_2OZ_1$, wherein $Z_1$ is a group selected from alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether;

$R'_3$ is $(C=O)Z_2$, wherein $Z_2$ is a group selected from alkyl, alkenyl, alkynyl, alkoxyalkyl, cycloalkyl, cycloalkenyl, cycloalkynyl, aryl, alkaryl, arylalkyl, or polyether; and/or the fluorophore is selected from a group consisting of acridine orange, anthracene ring, allophycocyanin, BODIPY, cyanines, coumarin, Edans, Eosin, Erythrosin, fluorescamine, fluorescein, FAM (carboxyfluorescein), HEX (hexachlorofluorescein), JOE (6-carboxy-4',5'-dichloro-2',7'-dimethoxy-fluorescein), Oregon Green, phycocyanin, phycoerythrin, rhodamine, ROX (Carboxy-X-rhodamine), TAMRA (carboxytetramethylrhodamine), TET (tetrachloro-fluorescein), Texas red, tetramethylrhodamine, and xanthines.

This invention also provides compounds that have high specificity and selectivity in the measurement of peroxynitrite. In one embodiment, the compounds have the following general formula (II):

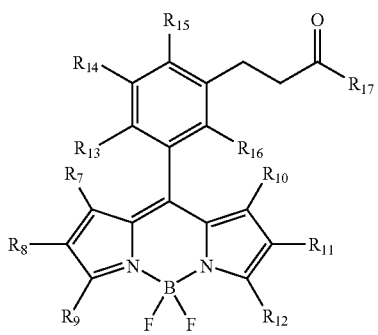

(II)

wherein:

R$_7$ and R$_{10}$ are independently hydrogen or a group selected from halogen, lower alkyl, lower alkenyl, halogenated alkyl, CN, or NO$_2$;

R$_8$, R$_9$, R$_{11}$, and R$_{12}$ are independently hydrogen, halogen, alkyl, halogenated alkyl, alkenyl or a group selected from keto, aldehyde, carboxylate, carboxylic ester, alkylamino, hydroxyl, alkoxy, alkoxyalkyl, polyether, alkylthio, cyano, nitro, or of the form (C=O)—Y or (C=O)—X—Y, wherein X is a lower alkyl or alkenyl chain, and Y is hydrogen or a group selected from alkyl, alkenyl, alkynyl, cycloalkyl, cycloalkenyl, cycloalkynyl, aryl, alkaryl, arylalkyl, keto, aldehyde, carboxylate, carboxylic ester, carbamate, amide, amino, alkylamino, hydroxyl, alkoxy, polyether, alkylthio, cyano, nitro, sulfonyl, inorganic ester, or a 5- to 7-membered heterocyclic ring whose ring atoms are selected from the group consisting of carbon, nitrogen, oxygen and sulfur, wherein the ring atoms further include 3 to 6 carbon atoms, and, typically, no more than two heteroatoms;

R$_{13}$ is OR'$_4$ or NR'$_5$R'$_6$, wherein R'$_4$, R'$_5$ and R'$_6$ are independently hydrogen or a group selected from alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether;

R$_{14}$ and R$_{15}$ are independently hydrogen, halogen, alkyl, alkoxy, polyether, or R$_{14}$ and R$_{15}$ come together to form a 5, 6, or 7-membered ring which is selected from aryl, heterocyclic, heteroaryl, or heteroaromatic;

R$_{16}$ is hydrogen, alkyl, alkoxy, or polyether; and

R$_{17}$ is an electron-withdrawing group selected from CF$_3$, halogen-substituted lower alkyl (e.g., CF$_n$H$_{3-n}$, wherein n is 1 or 2), or (C=O)—O—W$_2$, wherein W$_2$ is a group selected from alkyl, alkenyl, alkynyl, cycloalkyl, cycloalkenyl, cycloalkynyl, aryl, alkaryl, or arylalkyl.

In addition, the compounds having general formula (II) discussed above have the following further embodiments:

R$_9$ is (C=O)NR''$_1$R''$_2$, wherein R''$_1$ and R''$_2$ are alkyl (e.g., —(CH$_2$)$_k$—CH$_3$, wherein k=0-24, and —(CH$_2$)$_l$—CH$_3$, wherein l=0-24);

R$_8$ and R$_9$ come together to form a ring, preferably as a 5, 6, or 7-membered ring, to form a cycloalkyl, cycloalkenyl, cycloalkynyl, aryl, heterocyclic, heteroaryl or heteroaromatic;

R$_{12}$ is (C=O)NR''$_3$R''$_4$, wherein R''$_3$ and R''$_4$ are alkyl (e.g., —(CH$_2$)$_p$—CH$_3$, wherein p=0-24, and —(CH$_2$)$_q$—CH$_3$, wherein q=0-24);

R$_{11}$ and R$_{12}$ come together to form a ring, preferably as a 5, 6, or 7-membered ring, to form a cycloalkyl, cycloalkenyl, cycloalkynyl, aryl, heterocyclic, heteroaryl or heteroaromatic; and/or R'$_4$ is CH$_3$ or OCH$_2$OZ$_3$, wherein Z$_3$ is a group selected from alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether.

The compound represented by general formula (II) can exist as a salt. And physiologically acceptable water-soluble salts can be suitably used for the agent and the measuring method of this invention. Further, the compound represented by the general formula (II) in a free form or a salt thereof may exist as a hydrate or a solvate, and any of these substances fall within the scope of this invention. The types of solvents that form the solvates are not particularly limited. For example, solvents such as acetonitrile, ethanol, water, or acetonitrile-water mixture can be exemplified.

In another embodiment, compounds that have high specificity and selectivity in the measurement of peroxynitrile have the following general formula (III):

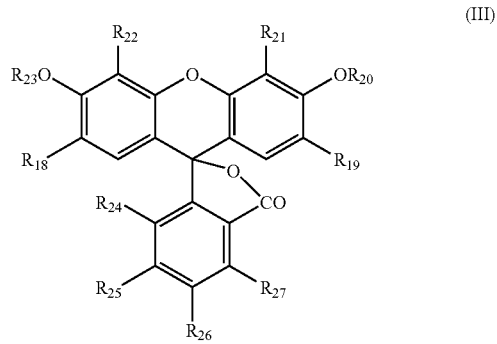

(III)

wherein:

R$_{18}$ and R$_{19}$ are independently hydrogen, halogen, alkyl, or alkoxy;

R$_{20}$ is hydrogen, alkyl, alkenyl, alkynyl, cycloalkyl, cycloalkenyl, cycloalkynyl, aryl, alkaryl, arylalkyl, carboxy alkyl, carboxylic ester, or aminoalkyl;

R$_{21}$ and R$_{22}$ are independently hydrogen or a group selected from alkyl, alkenyl, alkynyl, cycloalkyl, cycloalkenyl, cycloalkynyl, aryl, alkaryl, arylalkyl, keto, carboxy alkyl, carboxylate, carboxylic ester, carbamate, amide, amino, alkylamino, polyether, alkylthio, cyano, nitro, sulfonyl, or inorganic ester;

R$_{23}$ is selected from below:

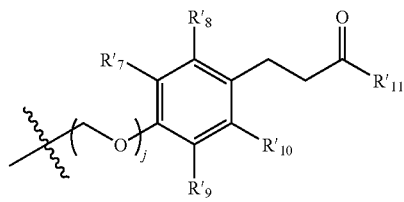

wherein j=0 or 1;

R'$_7$, R'$_8$, R'$_9$, and R'$_{10}$ are independently hydrogen or a group selected from halogen (e.g., Cl, Br, or I), alkyl (e.g., CH$_3$), alkoxy, alkyloxy, or polyether;

$R'_{11}$ is an electronic withdrawing group selected from $CF_3$, halogen-substituted lower alkyl (e.g., $CF_nH_{3-n}$, wherein n is 1 or 2), or (C=O)—O—$W_3$, wherein $W_3$ is a group selected from alkyl, alkenyl, alkynyl, cycloalkyl, cycloalkenyl, cycloalkynyl, aryl, alkaryl, or arylalkyl; and $R_{24}$, $R_{25}$, $R_{26}$, and $R_{27}$ are independently hydrogen or a group selected from alkyl, alkenyl, alkynyl, alkoxy, alkyloxy, cycloalkyl, cycloalkenyl, cycloalkynyl, aryl, alkaryl, arylalkyl, keto, aldehyde, carboxylate, carboxylic acid, carboxylic ester, carbamate, amide, amino, alkylamino, polyether, alkylthio, cyano, nitro, sulfonyl, inorganic ester, $R_{24}$ and $R_{25}$ come together to form a 5, 6, or 7-membered ring which is selected from cycloalkyl, cycloalkenyl, cycloalkynyl, aryl, heterocyclic, heteroaryl, or heteroaromatic, $R_{25}$ and $R_{26}$ come together to form a 5, 6, or 7-membered ring which is selected from cycloalkyl, cycloalkenyl, cycloalkynyl, aryl, heterocyclic, heteroaryl, or heteroaromatic, or $R_{26}$ and $R_{27}$ come together to form a 5, 6, or 7-membered ring which is selected from cycloalkyl, cycloalkenyl, cycloalkynyl, aryl, heterocyclic, heteroaryl, or heteroaromatic.

In addition, the compounds having general formula (III) discussed above have the following further embodiments:

$R'_7$ and $R'_8$ come together to form a 5, 6, or 7-membered ring which is selected from aryl, heterocyclic, heteroaryl, or heteroaromatic;

$R'_9$ and $R'_{10}$ come together to form a 5, 6, or 7-membered ring which is selected from aryl, heterocyclic, heteroaryl, or heteroaromatic;

$R_{20}$ is —$(CH_2)_m$—COOH, wherein m=1-24;

$R_{24}$ and $R_{25}$ come together to form a 5, 6, or 7-membered ring which is selected from cycloalkyl, cycloalkenyl, cycloalkynyl, aryl, heterocyclic, heteroaryl, or heteroaromatic;

$R_{25}$ and $R_{26}$ come together to form a 5, 6, or 7-membered ring which is selected from cycloalkyl, cycloalkenyl, cycloalkynyl, aryl, heterocyclic, heteroaryl, or heteroaromatic; and/or $R_{26}$ and $R_{27}$ come together to form a 5, 6, or 7-membered ring which is selected from cycloalkyl, cycloalkenyl, cycloalkynyl, aryl, heterocyclic, heteroaryl, or heteroaromatic.

The compound represented by general formula (III) can also exist as a salt. And physiologically acceptable water-soluble salts can be suitably used for the agent and the measuring method of this invention. Further, the compound represented by the general formula (III) in a free form or a salt thereof may exist as a hydrate or a solvate, and any of these substances fall within the scope of this invention. The types of solvents that form the solvates are not particularly limited. For example, solvents such as acetonitrile, ethanol, water or acetonitrile-water mixture can be exemplified.

It is found that peroxynitrite oxidizes some specific ketones represented by the general formula (I) in a way similar to the reaction with peroxymonosulfate, the commercial source of which is Oxone® ($2KHSO_5.KHSO_4.K_2SO_4$) (30-55% yield, 100% conversion) (FIG. 1). This reaction proceeds via a dioxirane intermediate. The dioxirane formation and its subsequent oxidation of phenol derivatives in an intramolecular fashion provide the basis for designing probes for the specific detection of peroxynitrite in cells. In addition, it is found that similar reactions do not proceed between the ketones and other reactive oxygen species or reactive nitrogen species present in the biological systems. It is further found that fluorescent probes for peroxynitrite can be synthesized by replacing some groups in the ketones with fluorophores. In one embodiment, the fluorescence properties of the BODIPY-based probes can be controlled by PET (photoinduced electron transfer) mechanism. Based on PM3 calculation method, fluorescent probes controlled by PET-dependent (photoinduced electron transfer) fluorescence off/on switching mechanism (FIG. 2) were designed. In another embodiment, before the oxidation with peroxynitrite, the fluorophore is masked and the probe is non-fluorescent. However, upon reaction with peroxynitrite, the fluorophore is released and become strongly fluorescent. For example, derivatization at the phenolic hydroxyl group of fluorescein/dichlorofluorescein can lead to significant decrease in fluorescent intensity. Thus, different fluorescein/dichlorofluorescein-based probes were designed. It is also found the substantially non-fluorescent compound represented by general formula (II) or (III) efficiently reacted with peroxynitrite under physiological conditions to give a strong fluorescent signal. Thus, peroxynitrite can be measured with very high specificity and selectivity by measuring the fluorescence of the oxidized fluorescent compound generated from the reaction between said non-fluorescent compound represented general formula (II) or (III) with peroxynitrite within the living cells or living tissues.

This invention also provides an agent for measuring peroxynitrite comprising any of the compounds mentioned above.

This invention also provides a method for measuring peroxynitrite in a chemical or biological sample (such as cells and tissues from animals or plants, and microorganism) comprising the steps:
a) contacting any of the compound mentioned above with the chemical or biological sample, and
b) measuring fluorescence of a resulting compound generated by a reaction between the compound and peroxynitrite present in the sample.

This invention also provides a high-throughput screening fluorescent method for detecting peroxynitrite comprising using the agent for measuring peroxynitrite mentioned above.

This invention also provides a high-throughput method for screening compounds that increase or decrease the production of peroxynitrite comprising using any of the compounds mentioned above.

General Synthetic Procedures

The compounds of this invention may be made by one skilled in organic synthesis by known techniques as well as by the general synthetic procedures disclosed herein. For example, some compounds represented by general formula (I) can be synthesized generally using procedures outlined by Yang et al (*J. Org. Chem*, 2000, 65, 4179-4184).

Figure 2:
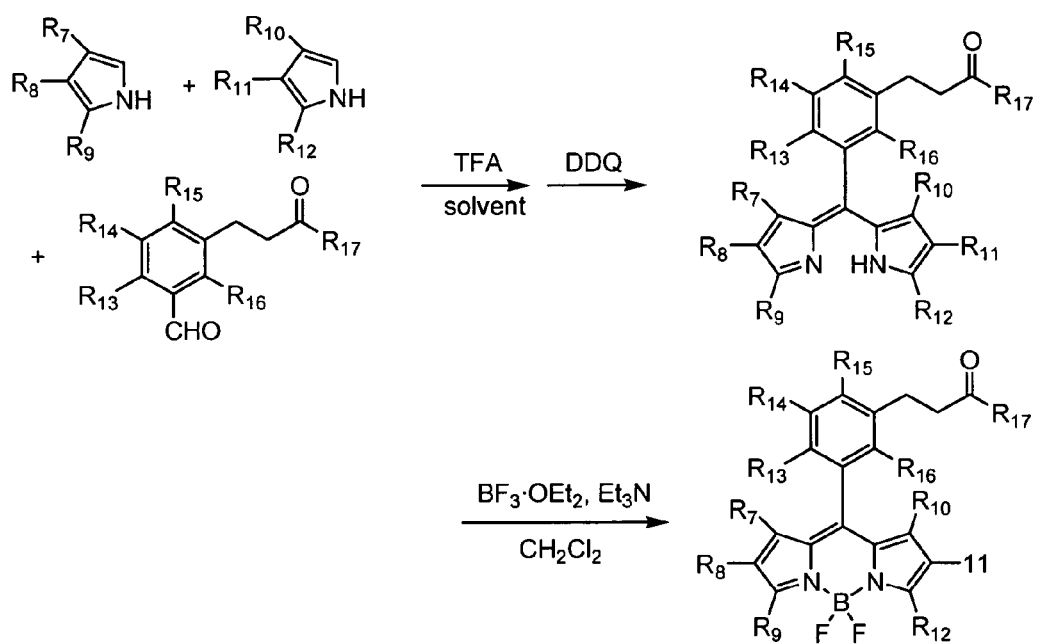
FIG. 2 shows the general synthetic schemes of the compound represented by general formula (II), wherein each of $R_i$ (i=7-17) is as defined in "Detailed Description Of The Invention".

A compound of general formula (II) can be synthesized generally by the following procedure (Nagano, T. et al., *J. Am. Chem. Soc.* 2004, 126, 3357-3367). The general synthetic schemes are shown in FIG. 2. The corresponding pyrrole part and aldehyde part are treated with a catalytic amount of TFA (trifluoroacetic acid) in an appropriate solvent such as dichloromethane or 1,2-dichloroethane at temperatures ranging from room temperature to 80° C. When TLC monitoring shows complete consumption of the corresponding aldehyde, a solution of DDQ (2,3-dichloro-5,6-dicyano-1,4-benzoquinone) is added, and stirring is continued for 15 to 30 mins. The pure intermediate can be isolated by work-up and column purification. Then the intermediate is treated with boron trifluoride etherate and triethylamine in dichloromethane. The solution is stirred at room temperature for 1 to 4 hours. A compound of this invention represented by the general formula (II) can be isolated by work-up followed by purification.

A preferred compound for performing the synthesis reaction is shown in the "Examples" section.

Among them, the corresponding pyrrole part and aldehyde part can be prepared independently, and some functional groups can be protected by protecting groups. The above synthetic schemes may be optimized sometimes by choosing the different protecting groups. Detailed explanations of protecting groups and skill of choosing a suitable protecting group can be found in, for example, a book entitled *Protective Groups in Organic Synthesis*, Greene, T. W., John Wiley & Sons, Inc., 1999.

Figure 3:
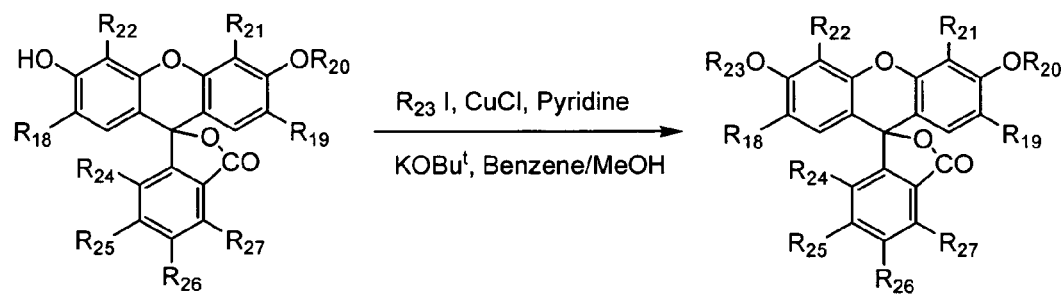
FIG. 3 shows the general synthetic schemes of the compound represented by general formula (III), wherein each of $R_i$ (i=18-27) is as defined in "Detailed Description Of The Invention".

A compound of general formula (III) can be synthesized generally by the following procedure (John, E. T. et al., *J. Chem. Soc., Perkin Trans I*, 1995, 1993; Mematt, M. et al., *Eur. J. Org. Chem.* 2001, 2535-2545; Rychnovsky, S.D. et al., *J. Am. Chem. Soc.* 1992, 114, 1677). The general synthetic schemes are shown in FIG. 3. The corresponding fluorescein derivative is treated with a solution of potassium tert-butoxide in an appropriate solvent such as a mixture of benzene and methanol. When the solid of fluorescein derivative dissolves completely, the solvent is evaporated in vacuo to give the corresponding potassium salt. Then, $R_{23}I$ wherein $R_{23}$ defined above in an appropriate solvent (such as pyridine) and CuCl are added. The resulting mixture is refluxed under Argon for 24 hours. After cooling to room temperature, a compound of this invention represented by the general formula (III) can be isolated by work-up followed by purification. A preferred compound for performing the synthesis reaction is shown in the "Examples" section.

Among them, the corresponding fluorescein derivatives and $R_{23}I$ can be prepared independently, and some functional groups can be protected by protecting groups. The same as the general synthetic schemes of compound represented by general formula (II), above synthetic schemes may be optimized sometimes by choosing different protecting groups.

The terms "work-up" and "purification" mean the combinations of techniques used in organic synthesis, e.g., washing, filtration, extraction, evaporation, distillation, crystallization, chromatography and the like. The intermediate may also be used in the subsequent reaction without purification.

EXAMPLES

The following Examples 1-4 are detailed descriptions of the methods of making and using the compounds represented by general formula (II). The detailed disclosure falls within the scope of, and serve to exemplify, the above described General Synthetic Procedures which form part of the invention. These Examples, as well as Examples 5-9, are presented for illustrative purposes only and are not intended to limit the scope of the invention.

Example 1

Synthetic Scheme of ss-6

Figure 4:
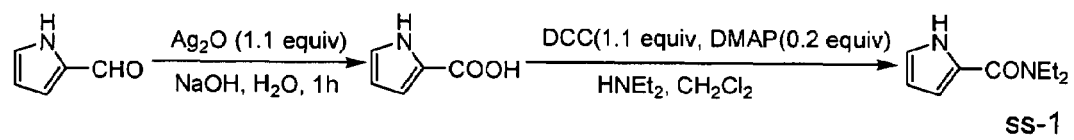
FIG. 4 to FIG. 7 show the synthetic schemes of Example 1.

1) Synthesis of pyrrole-2-carboxylic acid (Shown in FIG. 4)

Pyrrole-2-carboxaldehyde (10.0 g, 105 mmol) was dissolved in 50 mL of methanol then diluted by 500 mL of distilled water. Fresh silver oxide (48.3 g, 210 mmol) and sodium hydroxide (8.5 g, 212 mmol) were added. The reaction mixture was then stirred for one hour at root temperature. The precipitate was filtered off and washed with hot water. The combined filtrates and washings were extracted with diethyl ether (500 mL) and then acidified at 0° C. with 37% hydrochloric acid. The solution was extracted with diethyl ether (200 mL×4). The combined organic extract was dried over magnesium sulfate. The solvent was evaporated under reduced pressure to obtain pyrrole-2-carboxylic acid [634-97-9] (9.9 g, 85% yield).

2) Synthesis of N,N-diethyl-1H-pyrrole-2-carboxamide (ss-1) (shown in FIG. 4)

Pyrrole-2-carboxylic acid (10.0 g, 90 mmol) was dissolved in 250 mL of dichloromethane. DCC (N,N-dicyclohexylcarbodiimide) (20.4 g, 99 mmol), DMAP (4-dimethylaminopyridine) (2.2 g, 18 mmol) and diethylamine (10.2 mL, 99 mmol) were added subsequently at 0° C. under an Argon atmosphere. The reaction mixture was stirred at 0° C. for 30 mins then stirred at root temperature for 8 hours. The solution was diluted with dichloromethane and the solid was filtered off. The filtrates were washed by diluted hydrochloric acid, followed by saturated sodium bicarbonate solution. The organic layer was dried over sodium sulfate and then the solvent was evaporated under reduced pressure. The residue was purified by column chromatography on silica gel (eluent: ethyl acetate/n-hexane=1/2) to obtain N,N-diethyl-1H-pyrrole-2-carboxamide as a white solid (10.5 g, 70% yield). mp 78.6-79.9° C.; $^1$H NMR (300 MHz, CDCl$_3$): δ 10.1 (br, 1H), 6.94-6.88 (m, 1H), 6.57-6.51 (m, 1H), 6.26-6.21 (m, 1H), 3.95-3.86 (m, 4H), 1.31-1.24 (m, 6H); $^{13}$C NMR (75.5 Hz, CDCl$_3$): δ 161.9, 120.7, 111.3, 110.1, 109.5, 41.9, 13.4; IR (CH$_2$Cl$_2$) 3442, 2981, 2937, 1716, 1600 cm$^{-1}$; LRMS (EI) m/z (%) 166 (M$^+$; 100); HRMS (EI): calcd for C$_9$H$_{14}$N$_2$O: 166.1106, Found: 116.1106.

Figure 5:
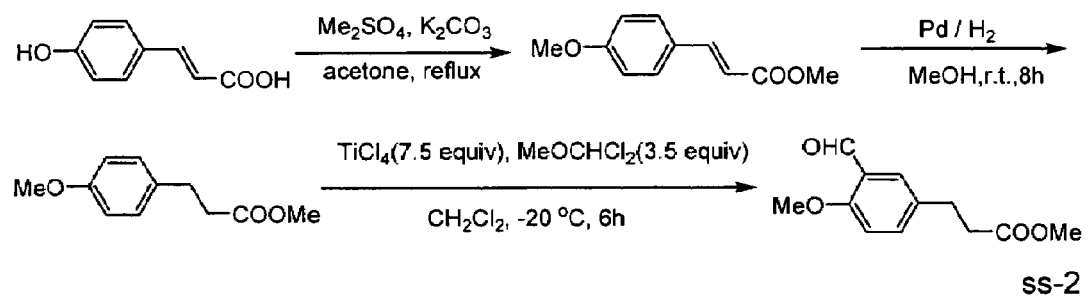

3) Synthesis of methyl-4-methoxycinnamate (shown in FIG. 5)

p-Hydroxycinnamic acid (10.0 g, 61 mmol) was dissolved in 200 mL of acetone. Potassium carbonate (58.7 g, 213 mmol) was added at room temperature. After 15 mins, dimethyl sulfate (16.4 mL, 213 mmol) was added at room temperature under Argon and then heated under reflux under an Argon atmosphere for 8 hours. The solid was filtered off and then 50 mL of water was added to the filtrates. The solvent was evaporated under reduced pressure and the mixture was extracted two times with 200 mL of ethyl acetate. The combined organic layer was dried over sodium sulfate and then the solvent was evaporated under reduced pressure. The residue was purified by column chromatography on silica gel (eluent: ethyl acetate/n-hexane=1/10) to obtain methyl-4-methoxycinnamate [832-01-9] (11.7 g, 99% yield).

4) Synthesis of methyl 3-(4-methoxyphenyl)propanoate (shown in FIG. 5)

Methyl-4-methoxycinnamate (11.7g, 61 mmol) was dissolved in 300 mL of methanol. Palladium (5% on activated carbon powder; 1.1 g) was added slowly under strong argon stream. Hydrogen gas was bubbled in and the reaction mixture was stirred vigorously for 2 hours. The solid was filtered off and the filtrates were dried over sodium sulfate. The solvent was evaporated under reduced pressure to obtain methyl 3-(4-methoxyphenyl)propanoate [15823-04-8] (11.7 g, 99%).

5) Synthesis of methyl 3-(3-formyl-4-methoxyphenyl)propanoate (ss-2) (shown in FIG. 5)

Methyl 3-(4-methoxyphenyl)propanoate (500 mg, 2.56 mmol) was dissolved in 30 mL of anhydrous dichloromethane. TiCl$_4$ (2.1 mL, 19 mmol) and MeOCHCl$_2$ (0.81 mL, 9.0 mmol) were added subsequently at −20° C. under Argon. The reaction mixture was stirred at −20° C. for 6 hours. Then the reaction mixture was slowly poured into a diluted hydrochloric acid solution. The dichloromethane layer was separated and washed with water followed by brine then dried over magnesium sulfate. The solvent was evaporated under reduced pressure. Then the crude residue was purified by column chromatography on silica gel (eluent: ethyl acetate/n-hexane=1/10) to obtain methyl 3-(3-formyl-4-methoxyphenyl)propanoate (ss-2) as a colorless oil (429 mg, 75% yield).

$^1$H NMR (400 MHz, CDCl$_3$): δ 10.4 (s, 1H), 7.65 (s, 1H), 7.40 (dd, J=6.3, 1.6 Hz, 1H), 6.92 (d, J=6.4 Hz, 1H), 3.91 (s, 3H), 3.66 (s, 3H), 2.92 (t, J=5.6 Hz, 2H), 2.61 (t, J=5.6 Hz, 2H); $^{13}$C NMR (100 MHz, CDCl$_3$): δ 189.7, 173.0, 160.4, 135.9, 132.7, 127.8, 124.6, 111.8, 55.7, 51.6, 35.4, 29.7; IR (CH$_2$Cl$_2$) 3055, 2945, 1734, 1682 cm$^{-1}$; LRMS (EI) m/z (%) 222 (M$^+$; 61), 149 (100); HRMS (EI): calcd for C$_{12}$H$_{14}$O$_4$: 222.0892, Found: 222.0892.

Figure 6:
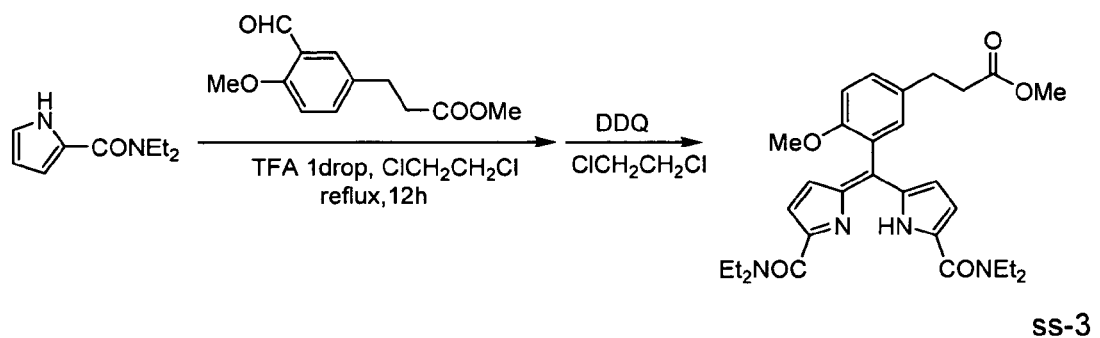

6) Synthesis of N,N-diethyl-5-[2-methoxy-5-(3-methoxy-3-oxopropyl)phenyl]-10H-dipyrrin-1,9-dicarboxamide (ss-3) (shown in FIG. 6)

Compound ss-1 (134 mg, 0.81 mmol) and ss-2 (90 mg, 0.41 mmol) were dissolved in 30 mL of anhydrous 1,2-dichloroethane under Argon atmosphere. One drop of TFA (trifluoroacetic acid) was added, and the solution was heated under reflux. When TLC monitoring (silica; CH2Cl2) showed complete consumption of the aldehyde, a solution of DDQ (2,3-dichloro-5,6-dicyano-1,4-benzoquinone) (189 mg, 0.81 mmol) in CH2Cl2 was added, and stirring was continued for 15 mins. The reaction mixture was washed with water, dried over MgSO4, filtered, and evaporated. The crude compound was purified by column chromatography on silica gel (eluent: ethyl acetate/dichloromethane/n-hexane=1/1/1) to afford compound ss-3 as a brown-red oil (289 mg, 67%). $^1$H NMR (400 MHz, CDCl$_3$): δ 7.27 (dd, J=8.4, 1.9 Hz, 1H), 7.07 (d, J=1.9 Hz, 1H), 6.92 (d, J=8.4 Hz, 1H), 6.62 (d, J=4.3 Hz, 2H), 6.45 (d, J=4.3 Hz, 2H), 3.72-3.60 (m, 14H), 2.93 (t, J=7.5 Hz, 2H), 2.64, (t, J=7.5 Hz, 2H), 1.30-1.23 (m, 12H); $^{13}$C NMR (75.5 MHz, CDCl$_3$): δ 172.8, 162.8, 155.7, 148.6, 141.7, 139.4, 131.5, 131.3, 129.8, 128.0, 125.1, 119.1, 111.0, 55.5, 51.3, 41.0 (br), 35.5, 29.6, 12.5 (br); IR (CH$_2$Cl$_2$) 3483, 2938, 1639 cm$^{-1}$; LRMS (EI) m/z (%) 534 (M$^+$; 21), 463 (100); HRMS (EI): calcd for C$_{30}$H$_{38}$N$_4$O$_5$: 534.2842, Found: 534.2842.

Figure 7:
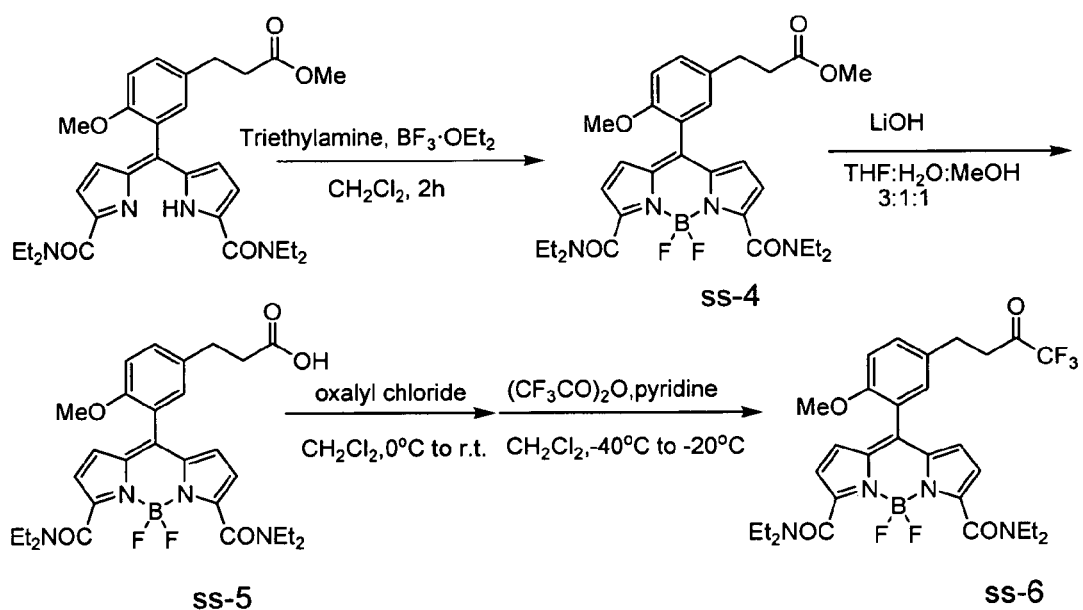

7) Synthesis of N,N-diethyl-8-[2-methoxy-5-(3-methoxy-3-oxopropyl)phenyl]-4,4-difluoro-4-bora-3a,4a-diaza-s-indacene-3,5-dicarboxamide (ss-4) (shown in FIG. 7)

Compound ss-3 (100 mg, 0.19 mmol) and triethylamine (0.73 mL, 5.2 mmol) were dissolved in 20 mL of absolute dichloromethane under an Argon atmosphere, and the solution was stirred at room temperature for 10 min. BF$_3$—OEt$_2$ (0.73 mL, 5.8 mmol) was added, and stirring was continued for 40 min. The reaction mixture was washed with water and 2N NaOH. The aqueous solution was extracted with CH2Cl2. The combined organic extracts were dried over Na2SO4, filtered, and evaporated. The crude compound was purified by column chromatography on silica gel (eluent: ethyl acetate/ dichloromethane=1/1) to afford compound ss-4 as orange crystals (74 mg, yield 70%). M.P. 77.0-77.9° C.; $^1$H NMR (400 MHz, CDCl$_3$): δ 7.33 (dd, J=8.2, 2.2 Hz, 1H), 7.12 (d, J=2.2 Hz, 1H), 6.98 (d, J=8.5 Hz, 1H), 6.78 (d, J=4.2 Hz, 2H), 6.44 (d, J=4.2 Hz, 2H), 3.73 (s, 3H), 3.66 (s, 3H), 3.58 (q, J=7.1 Hz, 4H), 3.29 (q, J=7.1 Hz, 4H), 2.95 (t, J=7.5 Hz, 2H), 2.64 (t, J=7.5 Hz, 2H), 1.25 (t, J=7.1 Hz, 6H), 1.10 (t, J=7.1 Hz, 6H); $^{13}$C NMR (100 MHz, CDCl$_3$): δ 172.7, 162.6, 155.4, 151.0, 145.1, 135.2, 131.9, 131.3, 131.2, 131.1, 121.9, 116.6, 111.3, 55.4, 51.4, 42.8, 38.4, 35.4, 29.5, 13.7, 11.9; $^{19}$F NMR (376.5 MHz, CDCl$_3$): δ−144.2 (m, J=30 Hz), −145.2 (m, J=30 Hz); IR (CH$_2$Cl$_2$) 2980, 1734, 1640 cm$^{-1}$; LRMS (EI) m/z (%) 582 (M$^+$; 21), 551 (100); HRMS (EI): calcd for C$_{30}$H$_{37}$BF$_2$N$_4$O$_5$: 582.2825, Found: 582.2831.

8) Synthesis of N,N-diethyl-8-(5-carboxyethyl-2-methoxyphenyl)-4,4-difluoro-4-bora-3a,4a -diaza-s-indacene-3,5-dicarboxamide (ss-5) (shown in FIG. 7)

Compound ss-4 (100 mg, 0.17 mmol) was dissolved in 3 mL of THF. Then 1 mL of methanol and 1 mL of distilled water were added. Lithium hydroxide monohydrate (22 mg, 0.52 mmol) was added and stirring was continued for 6 hours then 1 mL of brine was added. The solution was extracted three times with 10 mL of Et$_2$O. The combined organic extracts were dried over Na2SO4, filtered, and evaporated. The crude compound was employed in the subsequent reaction without further purification.

9) Synthesis of N,N-diethyl-8-[2-methoxy-(4,4,4-trifluoro-3-oxobutyl)phenyl]-4,4-difluoro-4-bora-3a,4a-diaza-s-indacene-3,5-dicarboxamide (ss-6) (shown in FIG. 7)

Crude compound ss-5 (560 mg, about 1.0 mmol) was dissolved in 20 mL of absolute dichloromethane. Oxalyl chloride and one drop of DMF were added subsequently at 0° C. under an Argon atmosphere. The reaction mixture was then stirred at root temperature for 30 min. The solvent was evaporated and the trace amount moisture and solvent was pumped off under high vacuum. Then the solid was dissolved in 20 mL of anhydrous dichloromethane again. Trifluoroacetic anhydride (0.84 mL, 6.0 mmol) and anhydrous pyridine (0.65 mL, 8.0 mmol) were added subsequently at −40° C. under an Ar atmosphere. The reaction mixture was then stirred at −20° C. for 4 hours. The reaction was quenched by adding 5 mL of water and the solution was extracted two times with 20 mL of dichloromethane. The combined organic extracts were dried over MgSO$_4$, filtered, and evaporated. The crude compound was purified by column chromatography on silica gel (eluent: ethyl acetate/dichloromethane=1/2) to afford compound ss-6 as red crystals (210 mg, about 34%). M.P. 83.6-84.6° C.; $^1$H NMR (300 MHz, CDCl$_3$): δ 7.32 (d, J=8.6 Hz, 1H) 7.12 (dd, J=6.5, 2.2 Hz, 1H), 6.96 (d, J=8.6 Hz, 1H), 6.73 (d, J=4.0 Hz, 2H), 6.43 (d, J=4.6 Hz, 2H), 3.73 (s, 3H), 3.59 (q, J=7.2 Hz, 4H), 3.31 (q, J=7.2 Hz, 4H), 3.06-3.00 (m, 2H), 2.83-2.77 (m, 1H), 2.03 (m, 1H), 1.25 (t, J=7.1 Hz, 6H), 1.09(t, J=7.1 Hz, 6H); $^{13}$C NMR (100 MHz, CDCl$_3$): δ 190.4 (q, J$_{C—F}$=35.4 Hz), 162.9, 155.8, 151.2, 145.0, 135.3, 131.4, 131.2, 122.3, 116.8, 111.6 (q, J$_{C—F}$=285 Hz), 55.6, 43.0, 38.7, 37.8, 36.1, 29.6, 27.2, 13.8, 12.0; $^{19}$F NMR (376.5 MHz, CDCl$_3$): δ−79.3 (m, J=11 Hz), −144.0 (m, J=30 Hz), −145.3 (m, J=30 Hz); IR (CH$_2$Cl$_2$) 2980, 1639, 1565 cm$^{-1}$; LRMS (EI) m/z (%) 620 (M$^+$; 30), 589 (100); HRMS (EI): calcd for C$_{30}$H$_{34}$BF$_5$N$_4$O$_4$: 620.2593, Found: 620.2598.

Example 2

1) Fluorescence Spectrum of ss-6

Figure 8:
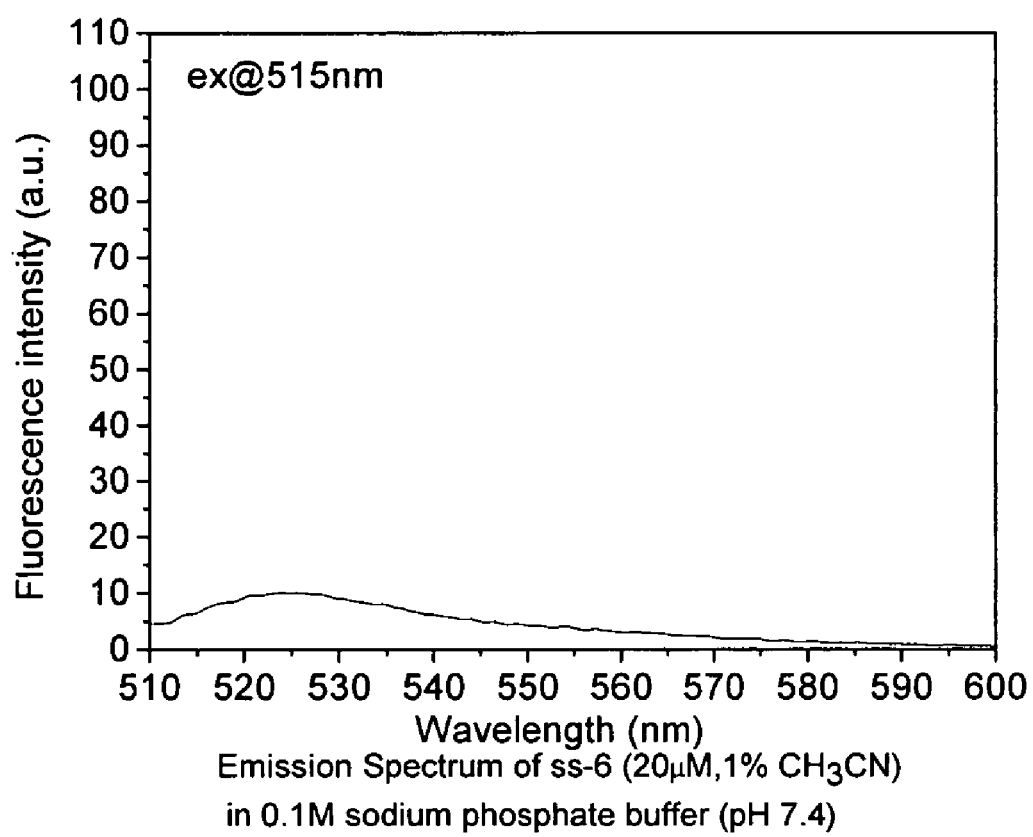
FIG. 8 shows a fluorescence spectrum of a 20 μM solution of the compound (ss-6) of this invention obtained in Example 1.

Compound ss-6 obtained in Example 1 was dissolved in CH$_3$CN to a concentration of 2 mM, and then the solution was added a 100 mM sodium phosphate buffer (pH 7.4) for dissolution to a final concentration of 20 μM. The excitation spectrum and the fluorescence spectrum of the 20 μM ss-6 solution were measured using a Perkin Elmer LS50 fluorescence spectrometer. Slit width was 5 nm for both the excitation spectrum and the fluorescence spectrum, and the photomultiplier voltage was 775 V. The measurement was carried out at the excitation wavelength of 515 nm. The results are shown in FIG. 8.

In order to investigate the reaction between ss-6 and peroxynitrite (ONOO−), a solution of ONOO− was prepared by the method of Keith and Powell (Keith, W. G. & Powell, R. E.; Kinetics of decomposition of peroxynitrous acid; *J. Chem. Soc. A*, 1969, 1, 90). Briefly, a mixture of sodium nitrite (0.6 mol/L), and hydrogen peroxide (0.7 mol/L) was acidified with hydrochloric acid (0.6 mol/L) and sodium hydroxide (1.5 mol/L) was added within 1-2 s to neutralize the acid and make the solution alkaline. The excess hydrogen peroxide was destroyed by passing the solution through manganese dioxide. The solution was then frozen. A dark yellow solution enriched in peroxynitrite was separated out and used in all experiments.

The peroxynitrite concentration in the stock solutions used was estimated by using an extinction coefficient of 1670 cm$^{-1}$ (mol/L)$^{-1}$ at 302 nm (Hughes and Nicklin; The chemistry of pernitrites. Part I. Kinetics of decomposition of pernitrous acid; *J. Chem. Soc. A*, 1968, 2, 450-452). The peroxynitrite solution prepared was usually very basic (pH 12). When larger volumes of peroxynitrite were added, part of the excess base was neutralized on the day of the experiment. This peroxynitrite solution of lower basicity was checked for its absorption at the beginning and the end of the study to ascertain that the peroxynitrite had not decomposed during the time required for incubations. The incubation tubes were also routinely checked to make sure that the final pH did not change after the addition of peroxynitrite.

Figure 9:
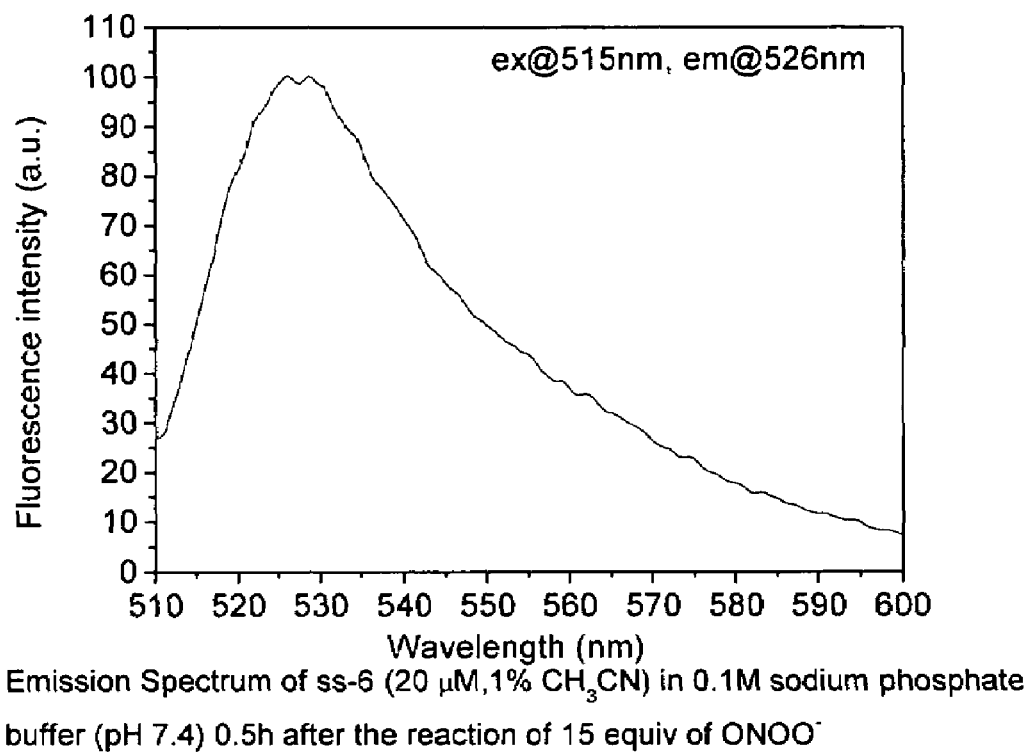
FIG. 9 shows a fluorescence spectrum of the solution 30 min after the reaction of 15 equiv of ONOO⁻ with 5 mL of 20 μM ss-6.

Subsequently, 15 equiv of ONOO− solution with different concentration was slowly added to a 20 μM ss-6 solution with vigorous stirring at room temperature. The volume change must be less than one percent. The changes in fluorescence intensity were measured after 30 min. The results are shown in FIG. 9. The excitation spectrum and the fluorescence spectrum of the solution after the completion of the reaction were measured using the same conditions as described above. Dramatic increase in fluorescence intensity was observed compared to FIG. 8.

2) UV-Vis Absorption Spectrum of ss-6

Figure 10:
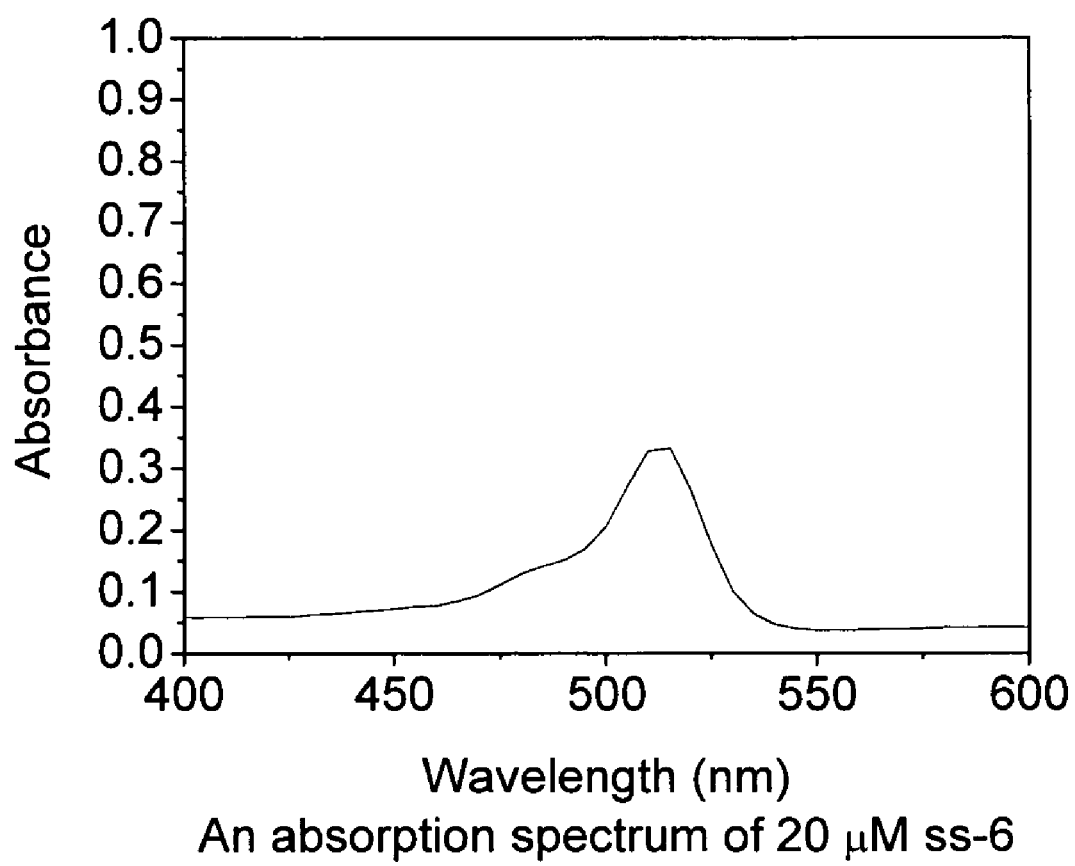
FIG. 10 shows an absorption spectrum of 20 μM ss-6.

Compound ss-6 was dissolved in dichloromethane to a concentration of 20 μM, the absorption spectrum of the resulting 20 μM ss-6 solution was measured. The results are shown in FIG. 10. The result verified that ss-6 had the absorption maximum at around 515 nm.

Example 3

Comparison of Specificity of ss-6 with Different Reactive Oxygen Species

Compound ss-6 obtained in Example 1 was dissolved in CH$_3$CN to a concentration of 2 mM, and then the solution was added with a 100 mM sodium phosphate buffer (pH 7.4) for dissolution at a final concentration of 20 μM. 50 μL of different reactive oxygen species (10 equiv) were added independently to 5 mL of the corresponding ss-6 solution. The changes in fluorescence intensity before and after the treatment were measured. The fluorescence intensity was measured under the same conditions as those in Example 2. Each concentration of the fluorescence probe was 20 μM (a 100 mM sodium phosphate buffer, pH 7.4). The results are shown in Table 1. It was verified from the result that ss-6 has very high selectivity.

TABLE 1

| Probe | ROS | | | | | |
|---|---|---|---|---|---|---|
| | ONOO− | SIN-1[a] | •OH[b] | $^1O_2$[c] | $O_2^{•-}$[d] | $H_2O_2$[e] |
| ss-6 | 750% | 166% | 2% | 3% | −1% | −5% |

[a]SIN-1 can generate ONOO− slowly in buffer.
[b]Fe(ClO$_4$)$_2$ (25 μL, 40 mM in buffer) and H$_2$O$_2$ (25 μL, 80 mM) were added.
[c][3-(1,4-dihydro-1,4-epidioxy-1-napthyl)propionic acid at 37° C. (50 μL, 20 mM) was added.
[d]Xanthine Oxidase was added firstly. After all XO dissolved, Xanthine (50 μL, 20 mM) was added.

Example 4

Specific Detection of Peroxynitrite with ss-6

Figure 11:
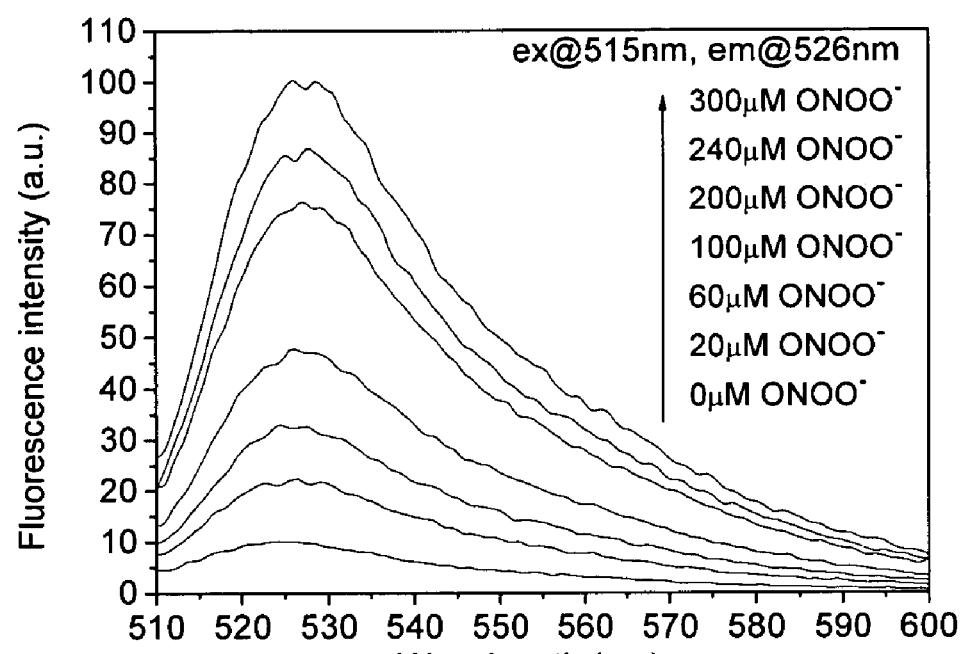
FIG. 11 shows fluorescence spectra taken 30 min after the reaction between ss-6 and ONOO⁻ with concentration ranging from 0 to 300 μM.
Figure 12:
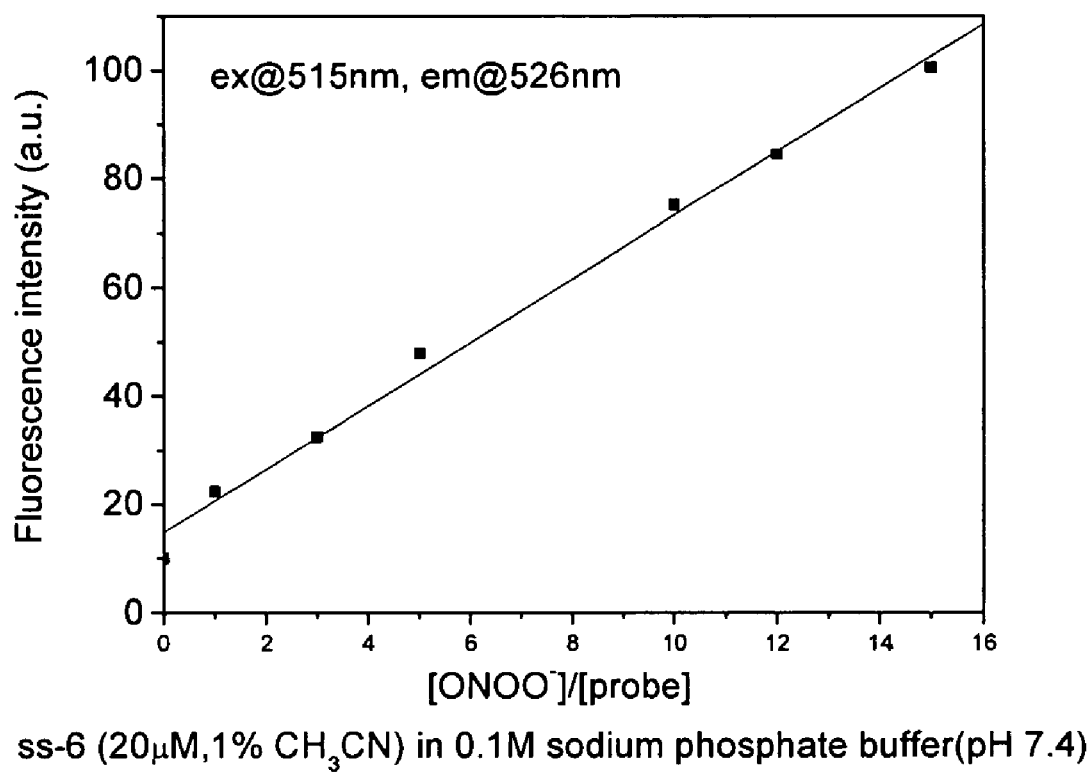
FIG. 12 shows the linear relationship between fluorescence intensity and the concentration of ONOO⁻.

Compound ss-6 obtained in Example 1 was dissolved in CH$_3$CN to a concentration of 2 mM, and then the solution was added with a 100 mM sodium phosphate buffer (pH 7.4) for dissolution at a final concentration of 20 μM. Then peroxynitrite was added to final concentrations of 0, 20, 60, 100, 200, 240 and 300 μM, and the fluorescence spectrum was measured after 30 mins. The fluorescence spectrum was measured under the same conditions as those in Example 2. The results were shown in FIG. 11. As clearly shown in FIG. 11, ss-6 gave great increase in fluorescence intensity, and the fluorescence intensity has good linear relationship with the concentration of ONOO− (shown in FIG. 12).

The following examples are detailed descriptions of the methods of making and using the compounds represented by general formula (III). The detailed disclosure falls within the scope of, and serve to exemplify, the above described General Synthetic Procedures which form part of the invention. These examples are presented for illustrative purposes only and are not intended to limit the scope of the invention.

Example 5

Synthetic Scheme of ss-12

Figure 13:
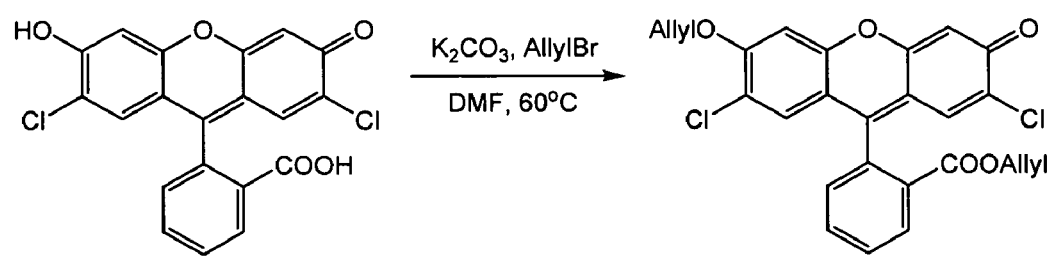
FIG. 13 to FIG. 18 show the synthetic schemes of Example 5.

1) Synthesis of ss-7 (shown in FIG. 13)

To a solution of 2,7-dichlorofluorescein (1.0 g, 2.5 mmol) in DMF (dimethylformamide) was added allyl bromide (0.47 mL, 5.0 mmol). After the reaction mixture was stirred at 60° C. for 3 hours, water was added and a red solid was formed. Compound ss-7 was obtained by filtration in >99% yield. $^1$H NMR (300 MHz, CDCl$_3$) δ 8.33 (d, J=7.6 Hz, 1H), 7.78 (t, J=7.3 Hz, 1H), 7.74 (t, J=7.3 Hz, 1H), 7.30 (d, J=7.3 Hz, 1H), 7.03 (d, J=2.8 Hz, 2H), 6.96 (s, 1H), 6.58 (s, 1H), 6.12-6.00 (m, 1H), 5.74-5.58 (m, 1H), 5.56-5.38 (m, 2H), 5.21-5.13 (m, 2H), 4.75 (d, J=6.2 Hz, 2H), 4.53 (d, J=5.8 Hz, 2H); $^{13}$C NMR (75 MHz, CDCl$_3$) δ 177.71, 164.54, 158.16, 157.79, 152.35, 149.52, 135.28, 133.55, 133.12, 131.59, 131.05, 130.97, 130.38, 130.27, 130.13, 128.03, 127.29, 120.43, 119.29, 119.08, 117.71, 115.04, 105.67, 101.14, 70.35, 66.10; IR (CH$_2$Cl$_2$) 1718, 1589 cm$^{-1}$; LRMS (EI) m/z (%) 480 (M$^+$; 100); HRMS (EI) for C$_{26}$H$_{17}$C$_{12}$O$_5$: calcd 480.0453, Found: 480.0447.

Figure 14:
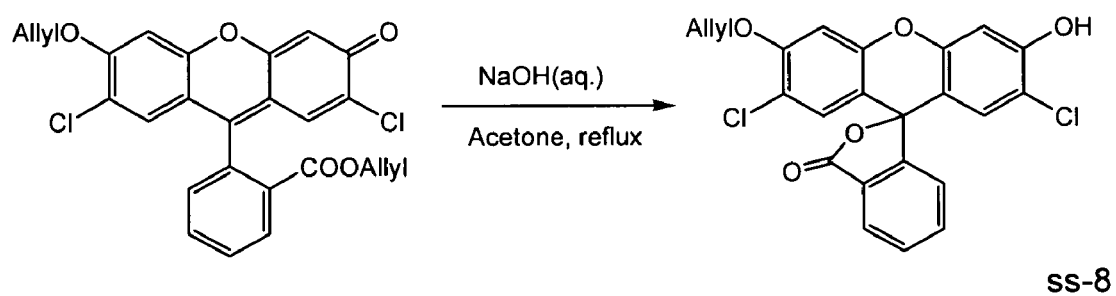

2) Synthesis of ss-8 (shown in FIG. 14)

Compound ss-7 (1.2 g, 2.5 mmol) was dissolved in a mixture of acetone (50 mL) and NaOH (1.25M; 50 mL). The solution was heated to reflux for 1 hour. After cooling to room temperature, 1N HCl was added to the reaction mixture to neutralize the solution to pH 2. Ethyl acetate was added to the extract. The organic layer was washed with brine, dried over sodium sulfate and evaporated in vacuo. The residue was purified by silica gel column chromatography to give compound ss-8 (760 mg, 68% yield). $^1$H NMR (400 MHz, CDCl$_3$) δ 8.30 (br, 1H), 8.07 (d, J=7.1 Hz, 1H), 7.72 (t, J=7.3 Hz, 1H), 7.68 (t, J=7.3 Hz, 1H), 7.16 (d, J=7.4 Hz, 1H), 6.91 (s, 1H), 6.80 (s, 1H), 6.73 (s, 1H), 6.71 (s, 1H), 6.10-6.03 (m, 1H), 5.48 (d, J=17.2 Hz, 1H), 5.36 (d, J=10.5 Hz, 1H), 4.12 (d, J=7.2 Hz, 2H); $^{13}$C NMR (100 MHz, CDCl$_3$) δ 168.27, 155.21, 155.04, 151.51, 150.30, 149.98, 135.96, 132.59, 130.59, 128.27, 128.09, 125.83, 125.18, 123.95, 118.10, 117.26, 116.44, 111.48, 110.34, 103.62, 102.39, 81.23, 69.53; IR (CH$_2$Cl$_2$) 2955, 1771, 1597 cm$^{-1}$; LRMS (EI) m/z (%) 440 (M$^+$; 3), 361 (100); HRMS (EI) for C$_{23}$H$_{14}$Cl$_2$O$_5$: calcd 440.0218, Found: 440.0222.

Figure 15:
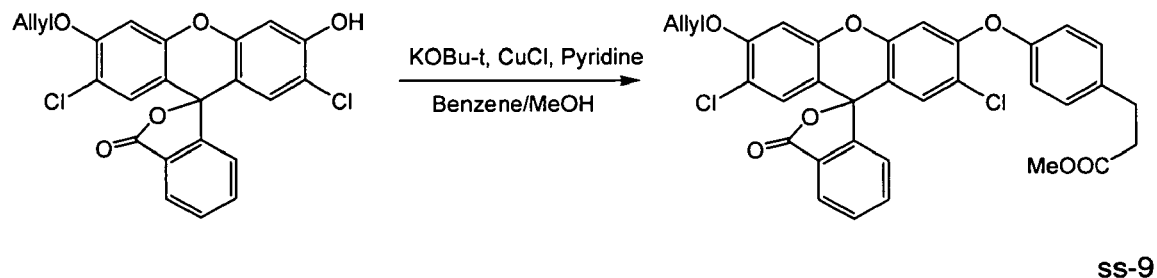

3) Synthesis of ss-9 (Shown in FIG. 15)

To a solution of potassium tert-butoxide (230 mg, 2.0 mmol) in a mixture of benzene (8 mL) and methanol (3 mL) was added ss-8 at room temperature. When the solid had dissolved completely, the solvent was evaporated in vacuo to give the corresponding potassium salt. Then CuCl (204 mg, 1.9 mmol) and compound ss-8 (980mg, 3.4 mmol) in pyridine (9 mL) were added in. The resulting mixture was refluxed under Argon for 24 hours. After cooling to room temperature, the reaction mixture was acidified with aqueous HCl. The mixture was extracted with ethyl acetate. The organic layer was washed with brine, dried over sodium sulfate and evaporated in vacuo. The residue was purified by silica gel column chromatography to give ss-9 (200 mg, 20% yield). $^1$H NMR (300 MHz, CDCl$_3$) δ 8.07 (d, J=6.6 Hz, 1H), 7.74 (t, J=7.3 Hz, 1H), 7.71 (t, J=7.3 Hz, 1H), 7.24 (d, J=8.3 Hz, 2H), 7.18 (d, J=7.0 Hz, 1H), 7.00 (d, J=8.4 Hz, 2H), 6.82 (s, 1H), 6.74 (s, 1H), 6.73 (s, 1H), 6.71 (s, 1H), 6.08-6.01 (m, 1H), 5.46 (d, J=17.2 Hz, 1H), 5.34 (d, J=10.5 Hz, 1H), 4.62 (d, J=5.0 Hz, 211), 3.70 (s, 3H), 2.98 (t, J=7.5 Hz, 2H), 2.66 (t, J=7.5 Hz, 2H); $^{13}$C NMR (75 MHz, CDCl$_3$) δ 173.16, 168.74, 155.62, 155.33, 153.67, 151.91, 150.43, 150.37, 137.21, 135.51, 131.65, 130.38, 129.94, 129.36, 128.74, 126.34, 125.50, 123.81, 119.78, 118.83, 118.47, 115.29, 114.10, 111.32, 106.29, 101.52, 81.53, 69.83, 51.68, 35.64, 30.19; IR (CH$_2$Cl$_2$) 3055, 2928, 1765, 1589, 1475, 1412 cm$^{-1}$; LRMS (EI) m/z (%) 602 (M$^+$, 100); HRMS (EI) calcd for C$_{33}$H$_{24}$Cl$_2$O$_7$: 602.0899, Found: 602.0890.

Figure 16:
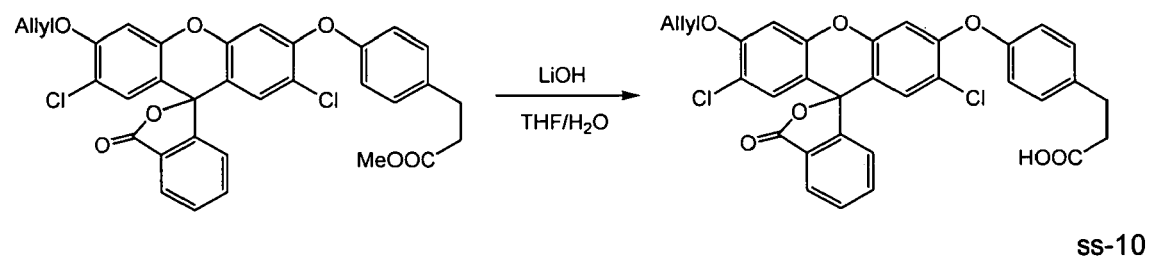

4) Synthesis of ss-10 (Shown in FIG. 16)

To a solution of compound ss-9 (874 mg, 1.44 mmol) in THF (10 mL) and water (3 mL) was added LiOH.H$_2$O (300 mg, 7.2 mmol) at room temperature. After stirring at 40° C. for 3 hours, the reaction mixture was acidified with 1 N HCl. The solution was saturated with NaCl and extracted with ethyl acetate. The combined organic layer was dried over anhydrous sodium sulfate and concentrated to afford ss-10 (500 mg, 60% yield). $^1$H NMR (400 MHz, CDCl$_3$) δ 8.30 (br, 1H), 8.08 (d, J=7.3 Hz, 1H), 7.74 (t, J=7.3 Hz, 1H), 7.70 (t, J=7.3 Hz, 1H), 7.26 (d, J=8.3 Hz, 2H), 7.18 (d, J=7.0 Hz, 1H), 7.01 (d, J=8.4 Hz, 2H), 6.82 (s, 1H), 6.74 (s, 1H), 6.73 (s, 1H), 6.71 (s, 1H), 6.06-6.00 (m, 1H), 5.46 (d, J=17.2 Hz, 1H), 5.33 (d, J=10.5 Hz, 1H), 4.61 (d, J=5.0 Hz, 2H), 2.99 (t, J=7.5 Hz, 2H), 2.72 (t, J=7.5 Hz, 2H); $^{13}$C NMR (75 MHz, CDCl$_3$) δ 177.77, 168.81, 155.67, 155.30, 154.83, 151.93, 150.46, 150.42, 136.87, 135.55, 131.67, 130.42, 129.97, 129.41, 128.78, 126.38, 125.55, 123.83, 119.80, 118.89, 118.50, 115.37, 114.21, 111.35, 106.42, 101.56, 81.59, 69.87, 35.76, 29.93; IR (CH$_2$Cl$_2$) 3421, 3055, 1765, 1624, 1416 cm$^{-1}$; FAB m/z 589 (M+); HRMS (EI) for C$_{32}$H$_{22}$Cl$_2$O$_7$: calcd 589.0821, Found 589.0820.

Figure 17:
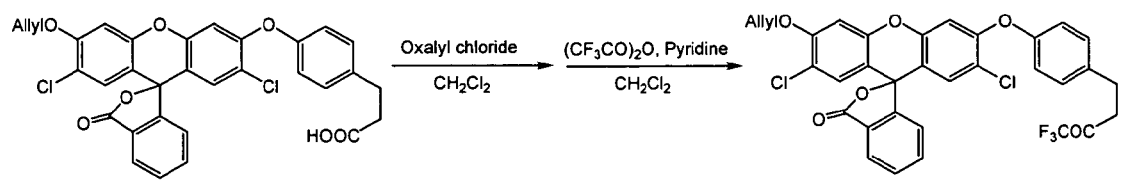

5) Synthesis of ss-11 (Shown in FIG. 17)

To a solution of compound ss-10 (490 mg, 0.83 mmol) in CH$_2$Cl$_2$ (15 mL) was added oxalyl chloride (0.22 mL, 2.5 mmol) and the solution was stirred at root temperature for 3 hours. The solvent and excess oxalyl chloride were evaporated off under reduced pressure. The resulting acid chloride was dissolved in CH$_2$Cl$_2$ (20 mL), followed by the addition of trifluoroacetic anhydride (0.7 mL, 5 mmol) and pyridine (0.54 mL, 7 mmol) at –40° C. under nitrogen. The resulting mixture was allowed to warm slowly to –20° C. and kept stirring at that temperature for 4 hours. The reaction was quenched by slow addition of water. The reaction mixture was washed with brine. The organic layer was dried over anhydrous sodium sulfate and concentrated. The residue was purified by flash column chromatography to give ss-11 as a yellow solid (240 mg, 45% yield). M.P. 85.0-86.1° C.; $^1$H NMR (400 MHz, CDCl$_3$) δ 8.08 (d, J=7.4 Hz, 1H), 7.76-7.68 (m, 2H), 7.26 (d, J=8.5 Hz, 2H), 7.18 (d, J=7.4 Hz, 1H), 7.02 (d, J=8.4 Hz, 2H), 6.83 (s, 1H), 6.74 (s, 1H), 6.73 (s, 1H), 6.71 (s, 1H), 6.07-6.00 (m, 1H), 5.46 (d, J=17.2 Hz, 1H), 5.33 (d, J=10.5 Hz, 1H), 4.62 (d, J=4.4 Hz, 2H), 3.10-3.07 (m, 2H), 3.04-3.00 (m, 2H); $^{13}$C NMR (101 MHz, CDCl$_3$) δ 190.5 (q, J$_{C-F}$=35.3 Hz), 168.72, 155.67, 155.09, 154.12, 151.91, 150.43, 150.41, 135.79, 135.53, 131.66, 130.41, 129.97, 129.44, 128.76, 126.36, 125.52, 123.81, 120.07, 119.82, 118.92, 118.47, 115.70 (q, J$_{C-F}$=292 Hz), 114.41, 111.34, 106.60, 101.55, 81.49, 69.86, 37.99, 27.61; $^{19}$F (376 MHz, CDCl$_3$) δ–79.18; IR (CH$_2$Cl$_2$) 3055, 1765, 1597, 1475, 1402 cm$^{-1}$; LRMS (EI) m/z (%) 640 (M$^+$), 561 (100); HRMS (EI) for C$_{33}$H$_{21}$C$_{12}$F$_3$O$_6$; calcd 640.0665, Found: 640.0667.

Figure 18:
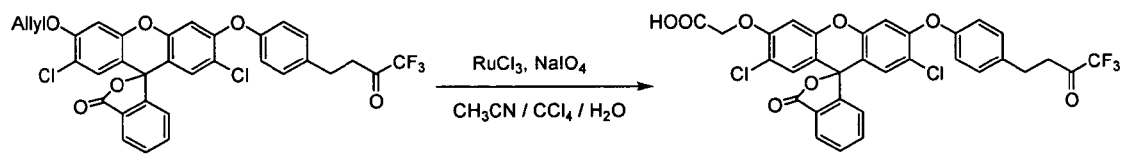

6) Synthesis of ss-12 (Shown in FIG. 18)

To a solution of compound ss-11 (260 mg, 0.4 mmol) in a mixture solvent of CH$_3$CN (4 mL), CCl$_4$ (4 mL) and water (6 mL) was added the catalyst RuCl$_3$.3H$_2$O (5 mg), followed by NaIO$_4$ (865 mg, 4.0 mmol). The mixture was stirred vigorously at room temperature for 1 hour before CH$_2$Cl$_2$ was added. The organic layer was separated and dried over anhydrous sodium sulfate and concentrated to give the residue. The residue was purified by flash column chromatography to give compound ss-12 (214 mg, 80% yield). M.P. 105.0-106.0° C.; $^1$H NMR (400 MHz, CDCl$_3$) δ 8.09 (d, J=7.2 Hz, 1H), 7.76-7.71 (m, 2H), 7.24 (d, J=8.5 Hz, 2H), 7.18 (d, J=7.4 Hz, 1H), 7.01 (d, J=8.5 Hz, 2H), 6.83 (s, 1H), 6.78 (s, 1H), 6.71 (s, 1H), 6.67 (s, 1H), 4.76 (d, J=2.5 Hz, 2H), 3.08 (t, J=6.2 Hz, 2H), 3.02 (t, J=6.2 Hz, 2H); $^{13}$C NMR (75 MHz, CDCl$_3$) δ 190.48 (q, J$_{C-F}$=35.3 Hz), 172.44, 168.82, 155.23, 154.72, 153.97, 151.77, 150.32, 150.24, 135.88, 135.64, 130.51, 129.99, 129.40, 129.24, 126.21, 125.59, 123.82, 120.16, 119.87, 118.94, 115.46 (q, J$_{C-F}$=292.2 Hz), 114.13, 112.71, 106.44, 101.67, 81.34, 65.49, 37.96, 27.57; IR ($CH_2Cl_2$) 3420, 3055, 1765, 1610, 1408 $cm^{-1}$; LRMS (EI) m/z (%) 614 ($M^+$—COOH; 19), 579 (100); HRMS (EI) for $C_{31}H_{18}C_{12}F_3O_6$: calcd 613.0433, Found: 613.0469.

Example 6

1) Fluorescence Spectrum of ss-12

Figure 19:
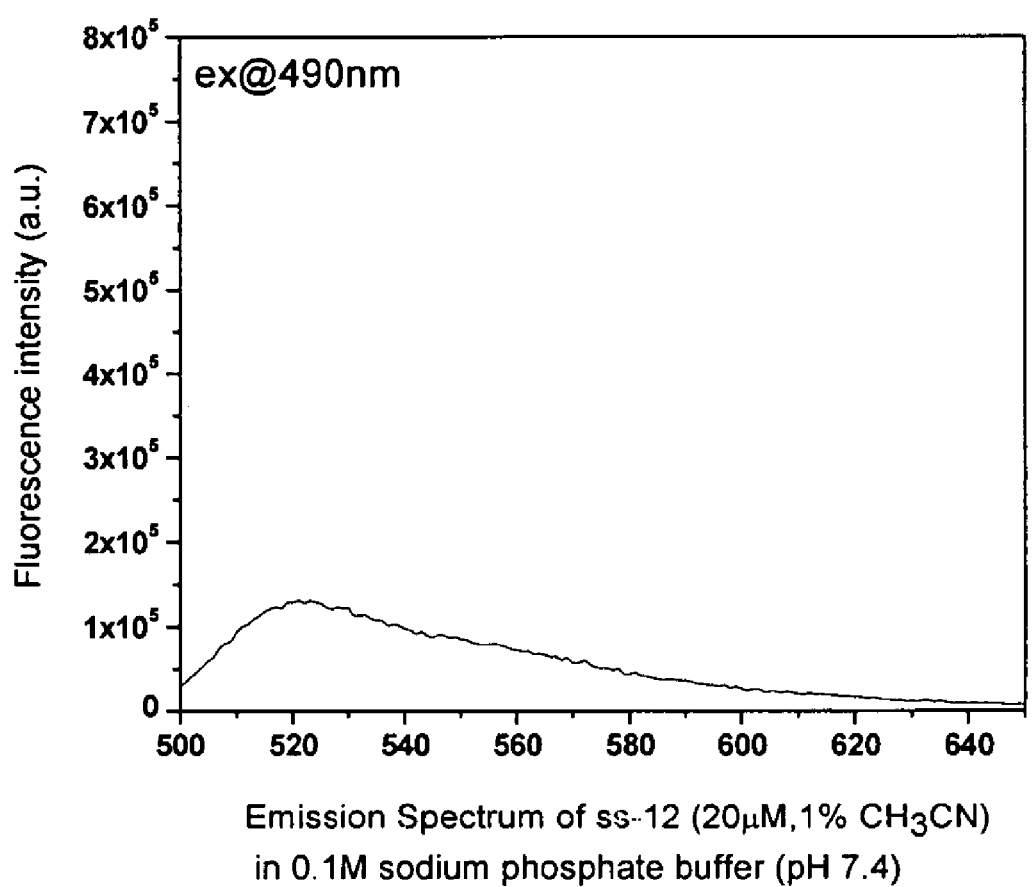
FIG. 19 shows a fluorescence spectrum of a 20 μM solution of the compound (ss-12) of this invention obtained in Example 5.

Compound ss-12 obtained in Example 5 was dissolved in $CH_3CN$ to a concentration of 2 mM, and then the solution was added a 100 mM sodium phosphate buffer (pH 7.4) for dissolution at a final concentration of 20 μM. The excitation spectrum and the fluorescence spectrum of the 20 μM ss-12 solution were measured using a Perkin Elmer® LS50 fluorescence spectrometer. Slit width was 2.5 nm for both the excitation spectrum and the fluorescence spectrum, and the photomultiplier voltage was 775 V. The measurement was carried out at the excitation wavelength of 490 nm. The results are shown in FIG. 19.

Figure 20:
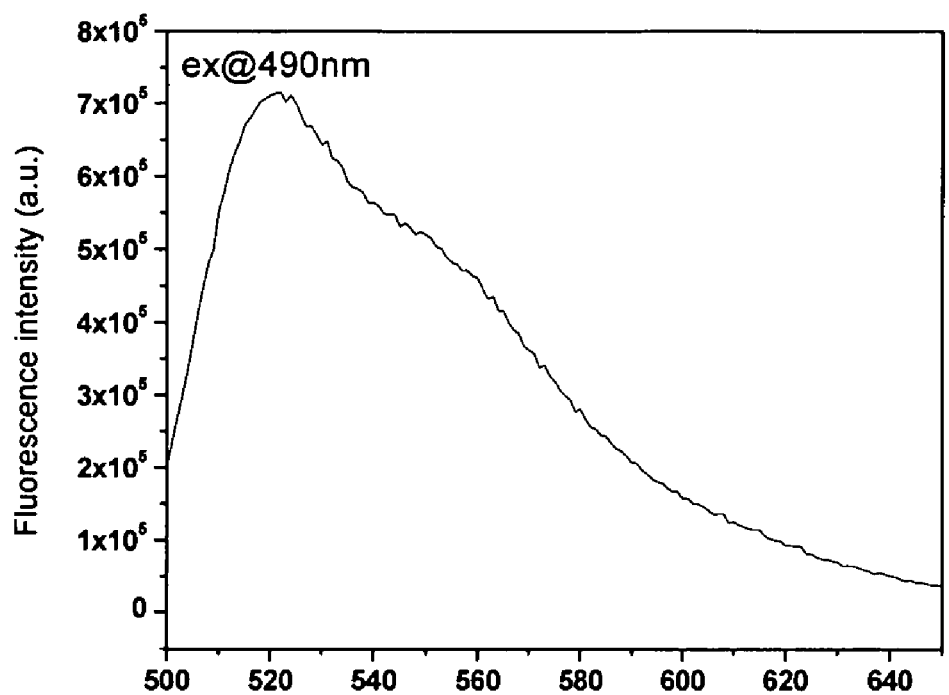
FIG. 20 shows a fluorescence spectrum of the solution 30 min after the reaction of 15 equiv of ONOO⁻ with 5 mL of 20 μM ss-12.

Subsequently, 15 equiv of $ONOO^-$ solution with different concentration was slowly added to a 20 μM ss-12 solution with vigorously stirring at room temperature. The volume change must be less than one percent. The changes in fluorescence intensity were measured after 30 min. The results are shown in FIG. 20. The excitation spectrum and the fluorescence spectrum of the solution after the completion of the reaction were measured using the same conditions as described above. Dramatic increase in fluorescence intensity was observed compared to FIG. 19.

2) UV-Vis Absorption Spectrum of ss-12

Figure 21:
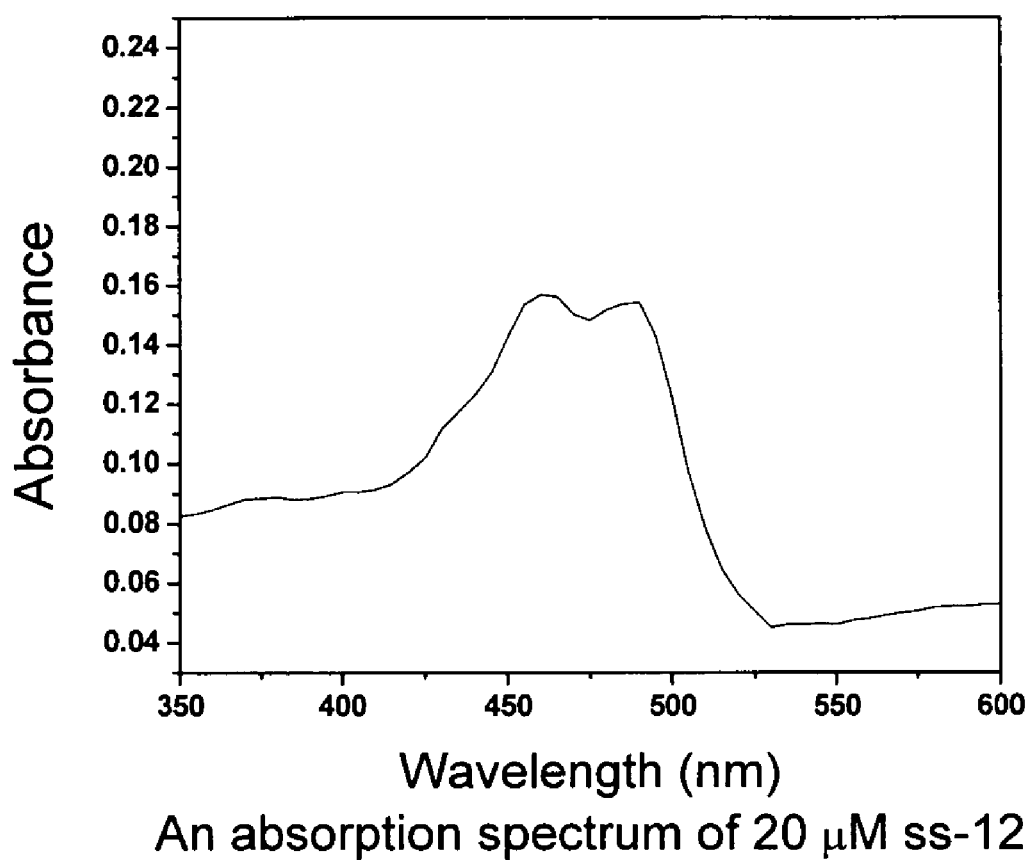
FIG. 21 shows an absorption spectrum of 20 μM ss-12.

Compound ss-12 was dissolved in dichloromethane to a concentration of 20 μM. The absorption spectrum of the resulting 20 μM ss-12 solution was measured. The results are shown in FIG. 21. The result showed that the ss-12 had two absorption peaks around 460 nm and 490 nm.

Example 7

Comparison of Specificity of ss-12 with Different Reactive Oxygen Species

Compound ss-12 obtained in Example 5 was dissolved in $CH_3CN$ to a concentration of 2 mM, and then the solution was added with a 100 mM sodium phosphate buffer (pH 7.4) for dissolution at a final concentration of 20 μM. 50 μL of different reactive oxygen species (10 equiv) were added independently to 5 mL of the corresponding ss-12 solution. The changes in fluorescence intensity before and after the treatment were measured. The fluorescence intensity was measured under the same conditions as those in Example 2. Each concentration of the fluorescence probe was 20 μM (a 100 mM sodium phosphate buffer, pH 7.4). The results are shown in Table 2. It was verified from the result that ss-12 has very high selectivity.

TABLE 2

| | ROS | | | | |
|---|---|---|---|---|---|
| Probe | $ONOO^-$ | $^1O_2{}^a$ | $O_2^{\bullet-a}$ | $H_2O_2{}^a$ | $^{\bullet}NO^b$ |
| ss-12 | 579% | 7% | 9% | −3% | 2% |

[a] Please see Example 3 Table 1 ROS generation procedure.
[b] NO was generated by SNP (Sodium Nitroferricyanide (III) Dihydrate) (Feelisch M., Eur Heart J. 1993, 14, 123-132.)

Example 8

Specific Detection of Peroxynitrite with ss-12

Figure 22:
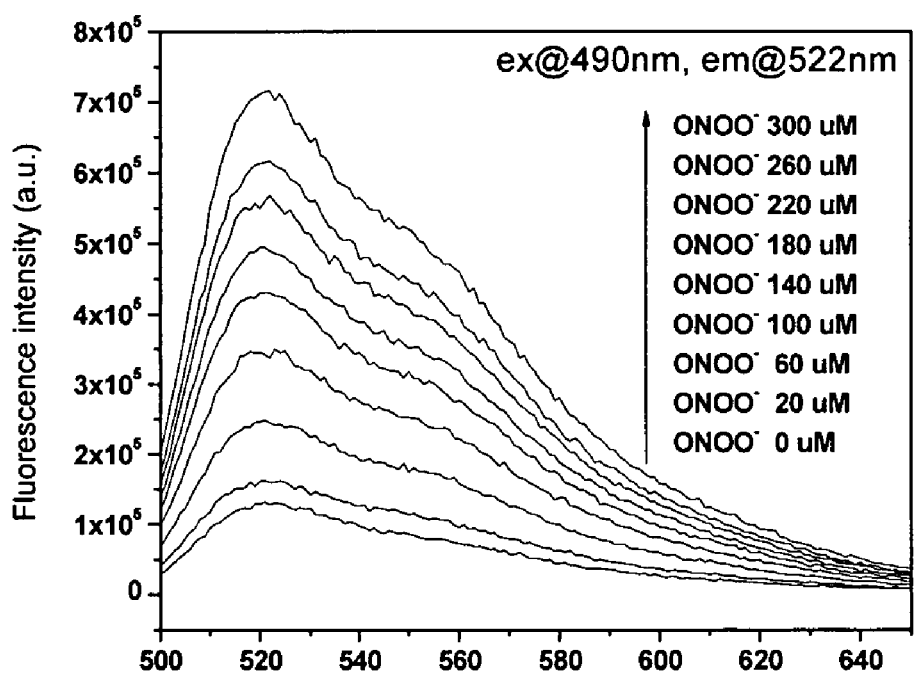
FIG. 22 shows fluorescence spectra taken 30 min after the reaction between ss-6 and ONOO⁻ with concentration ranging from 0 to 300 μM.
Figure 23:
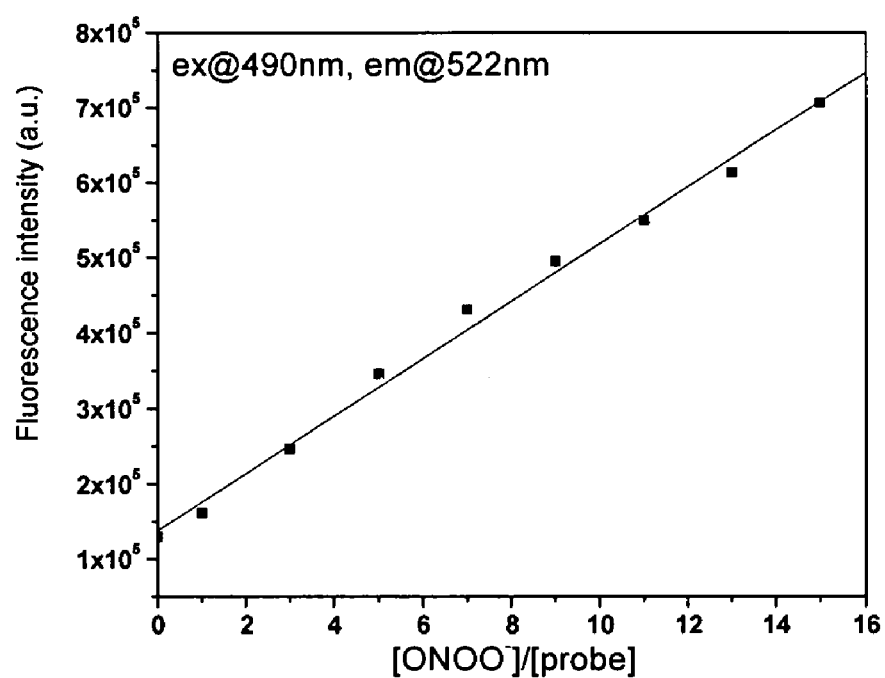
FIG. 23 shows the linear relationship between fluorescence intensity and the concentration of ONOO⁻.

Compound ss-12 obtained in Example 5 was dissolved in $CH_3CN$ to a concentration of 2 mM, and then the solution was added with a 100 mM sodium phosphate buffer (pH 7.4) for dissolution at a final concentration of 20 μM. Then peroxynitrite was added to final concentrations of 0, 20, 60, 100, 200, 240 and 300 μM, and the fluorescence spectrum was measured after 30 mins. The fluorescence spectrum was measured under the same conditions as those in Example 6. The results were shown in FIG. 22. As clearly shown in FIG. 22, ss-12 gave great increase in fluorescence intensity, and the fluorescence intensity has good linear relationship with the concentration of $ONOO^-$ (shown in FIG. 23).

Example 9

Cell Assay

Figure 24:
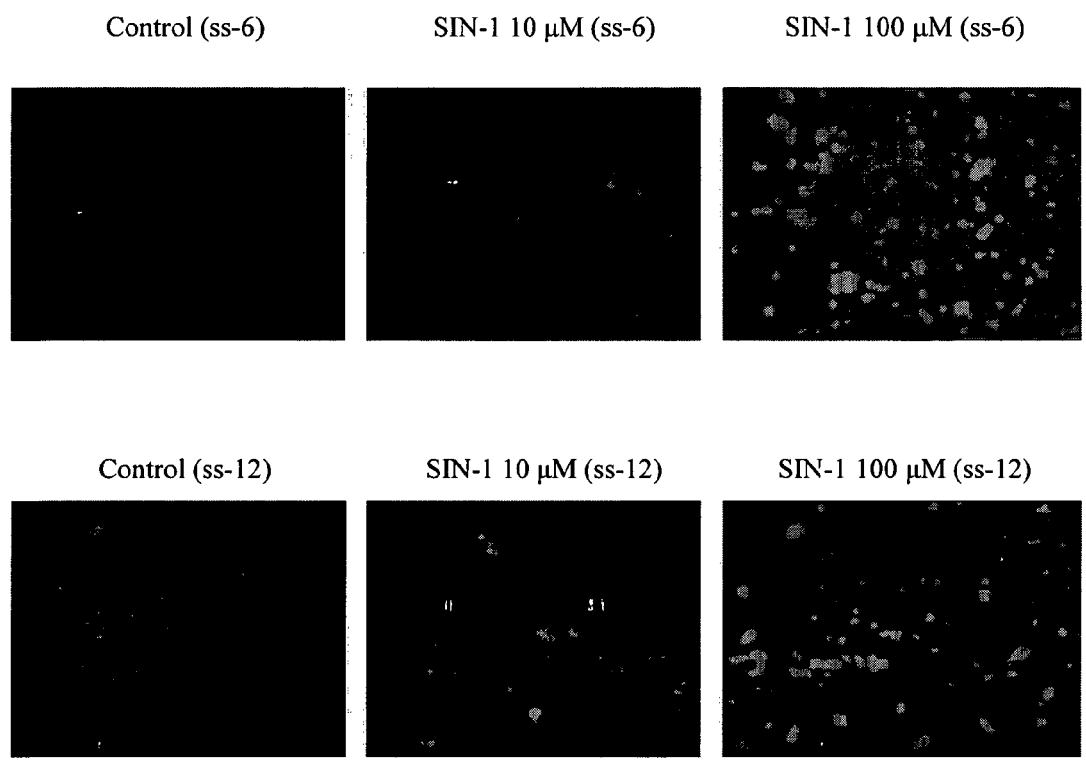
FIG. 24 shows fluorescent microscopy results of primary cultured neuronal cells that were incubated with ss-6 and ss-12 at a concentration of 20 μM, and then treated with 10 μM and 100 μM SIN-1 (3-Morpholino-sydnonimine-HCl).

Throughout this study, primary cultured cortex neurons were prepared from embryonic day 15 Sprague-Dawley rats. Briefly, dissociated cell suspensions were plated at a density of $2\times10^6$ cells/well on poly-L-lysine-coated 6-well plates (BD Biosciences, San Diego, Calif., USA) with Neurobasal/ 2% B27 (Gibco-BRL, Grand Island, N.Y.) containing glutamine (0.5 mM, Sigma Chemical Company, St. Louis, Mo.), penicillin (100 U/mL) and streptomycin (100 μg/mL). The cells were maintained in a humidified incubator at 37° C., in 5% $CO_2$-95% air. On the tenth day, cultured cortical cells were used for experimentation. The primary cultured neuronal cells were incubated with the ss-6 and ss-12 at the concentration of 20 μM for 15 mins and then washed with sodium phosphate buffer (100 mM, pH 7.4) for 3 times. After that, the cells were treated with 10 and 100 μM SIN-1 (3-Morpholino-sydnonimine-HCl) for 15 mins. After washed with sodium phosphate buffer (100 mM, pH 7.4), the cells were observed under fluorescent microscopy. The results show that the probes give satisfactory results for the measurement of intracellular ONOO— production (shown in FIG. 24)

REFERENCES

1. PCT International Publication No. WO 01/64664, published Sep. 7, 2001 (Nagano et al.)
2. PCT International Publication No. WO2004040296, published May 31, 2004 (Nagano et al.)
3. Augusto, O.; Radi, R. Gatti, R. M.; Vasquez-Vivar, *J. Methods Enzymol.* 1996, 269, 346-354.
4. Beal, M. F., *Free Radical Biol. & Med.* 2002, 32, 392.
5. Beckman, J. S., *Am. J. Physiol. Cell Physiol.* 1996, 271, C1424.
6. Beckman, J. S., Ischiropoulos H, Zhu L, van der Woerd M, Smith C, Chen J, Harrison J, Martin J. C. and Tsai M., *Arch Biochem Biophys,* 1992, 298, 438-445.
7. Crow, J. P., *Nitric Oxide.* 1997, 1, 145-157.
8. Cuzzocrea, S.; Riley, D. P.; Caputi, A. P.; Salvemini, D., *Pharmacol Rev.* 2001, 53, 135.
9. Feelisch M. *Eur Heart J.* 1993, 14, 123-132.
10. Gatti, R. M.; Alvarez, B.; Vasquez-Vivar, J.; Radi, R.; Augusto, O., *Arch. Biochem. Biophys.* 1998, 349, 36-46.
11. Gatti, R. M.; Radi, R.; Augusto, O., *FEBS Lett,* 1994, 348, 287-290.
12. Groves, J. T., *Curr. Opin. Chem. Biol.* 1999, 3, 226.
13. Gryglewski, R., *Nature* 1986, 320, 454.

14. Hughes, M. N.; Nicklin, H. G., *J. Chem. Soc. A* 1968, 450-452.
15. Ischiropoulos, H., *Arch. Biochem. Biophys.* 1998, 356, 1-11.
16. Ischiropoulos, H.; Gow, A.; Thom, S. R.; Kooy, N. W.; Royall, J. A.; Ceow, J. P., *Methods Enzymol.* 1999, 301, 367-373.
17. John E. T. Corrie, David R. Trentham, *J. Chem. Soc., Perkin Trans I,* 1995, 1993.
18. Kaur, H.; Halliwell, B., *FEBS Lett.* 1994, 350, 9-12.
19. Keith, W. G; Powell, R. E., *J. Chem. Soc. A,* 1969, 1, 90.
20. Kooy, N. W.; Royall, J. A.; Ischiropoulos, H.; Beckman, J. S., *Free Radic. Biol. Med.* 1994, 16, 149-156.
21. Kooy, N. W.; Royall, J. A.; Ischiropulos, H., *Free Radic. Biol. Res.* 1997, 27, 245-254.
22. Koppenol, W. H., *Redox Report* 2001, 6, 339-341
23. Lipton, S. A.; Chol, Y-B.; Pan, Z.-H.; Lei, S.-Z.; Chen, H.-S. V.; Sucher, N. J.; Loscaizo, J.; 24. Singel, D. J.; Stamier, J. S., *Nature* 1993, 364, 626.
24. Memattt, M., Geert-Jan Boons., *Eur. J. Org. Chem.* 2001, 2535-2545.
25. MacMillan-Crow, L. A.; Crow, J. P.; Kerby, J. D.; Beckman, J. S.; Thomson, J. A., *Proc. Natl. Acad. Sci. USA* 1996, 93, 11853.
26. Miles, A. M.; Bohle, D. S.; Glassbrenner, P. A.; Hansert, B.; Wink, D. A.; Grisham, M. S., *J. Biol. Chem.* 1996, 271, 40-47.
27. Nagano, T.; Gabe, Y.; Urano, Y.; Kikuchi K.; Kojima H., *J. Am. Chem. Soc.* 2004, 126, 3357-3367.
28. Pappolla, M. A.; Chyan, Y.-J.; Poeggeler, B.; Frangione, B.; Wilson, G, Ghiso, J.; Reiter, R. J., *J. Neural Transm.* 2000, 107, 203.
29. Radi, R., *Chem. Res. Toxicol.* 1998, 11, 720-721.
30. Radi, R.; Beckman, J. S.; Bush, K. M.; Freeman, B. A., *Arch. Biochem. Biophys.* 1991, 288, 481.
31. Radi R, Beckman, J. S., Bush, K. M. and Freeman B. A., *J. Biol. Chem,* 1991, 266, 4244-4250.
32. Radi, R.; Peluffo, G.; Alvarez, M. N.; Naviliat, M.; Cayota, A., *Free Radical Biol. & Med* 2001, 30, 463-488.
33. Rodenas, J.; Carbonell, T.; Mitjavila, M. T., *Free Radical. Biol. & Med.* 2000, 28, 374.
34. Romero, N.; Denicola, A.; Souza, J. M.; Radi, R., *Arch. Biochem. Biophys.* 1999, 368, 23-30.
35. Royall, J. A.; Ischiropoulos, H., *Arch. Biochem. Biophys.* 1993, J302, 348-355.
36. Rychnovsky, S. D., Skalitzky, D. J., Pathirana, C., Jensen, P. R., Fenical, W., *J. Am. Chem. Soc.* 1992, 114, 1677
37. Setsukinai, K.; Urano, Y.; Kakinuma, K.; Nagano, T., *J. Biol. Chem.* 2003, 278, 3170-3175.
38. Shi, H.; Noguchi, N.; Xu, Y.; Niki, E., *Biochem. Biophys. Res. Commun.* 1999, 257, 651.
39. Squadrito, G. L. and Pryor, W. A., *Free Radical Biol. & Med.* 1998, 25, 797.
40. Szabo, C., *Toxicol. Lett.* 2003, 140, 105.
41. Tarpey, M. M.; Fridovich, I., *Circ. Res.* 2001, 89, 224-236.
42. White, C. R.; Brock, T. A.; Chang, L. Y.; Crapo, J.; Briscoe, P.; Ku, D.; Bradley, W. A.; Gianturio, S. H.; Gore, J.; Freeman, B. A.; Tarpey, M. M., *Proc. Natl. Acad. Sci. USA* 1994, 91, 1044.
43. Yang, D.; Wong, M.-K.; Yan, Z., *J. Org. Chem,* 2000, 65, 4179-4184.
44. *Handbook of Fluorescent Probes and Research Products,* 9th Edition, Molecular Probes, Eugene, Oreg., Haughland, 2003.
45. *Protective Groups in Organic Synthesis,* Greene, T. W., John Wiley & Sons, Inc., 1999.

What is claimed is:

1. A compound which specifically reacts with peroxynitrite rather than $\cdot OH$, $H_2O_2$, $HOCl$, $^1O_2$, $NO_2^-$, $NO_3^-$, $NO$, $O_2^{\cdot -}$ or $ROO\cdot$ represented by the following general formula (I), (II), or (III), or a salt thereof:

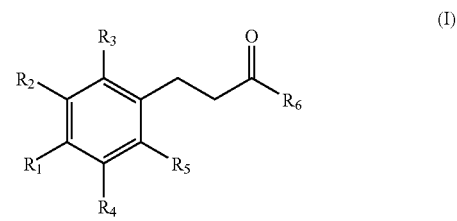

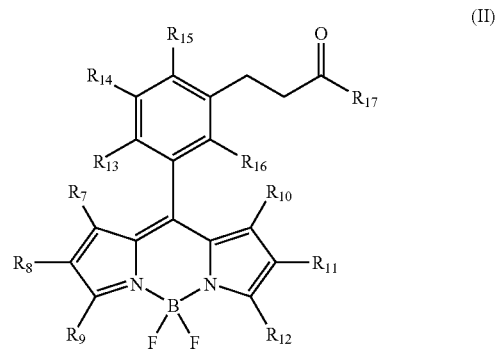

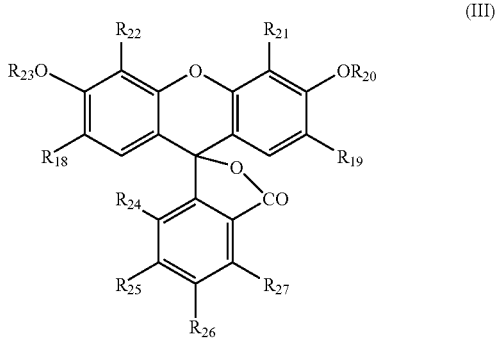

wherein:
- $R_1$ is $OR'_1$ or $NR'_2R'_3$, wherein $R'_1$, $R'_2$ and $R'_3$ are independently hydrogen, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether;
- $R_2$, $R_3$, $R_4$, and $R_5$ are independently hydrogen, halogen, alkyl, alkoxy, polyether, $R_2$ and $R_3$ come together to form a 5, 6, or 7-membered ring which is selected from aryl, heterocyclic, heteroaryl, or heteroaromatic, or $R_4$ and $R_5$ come together to form a 5, 6, or 7-membered ring which is aryl, heterocyclic, heteroaryl or heteroaromatic;
- $R_6$ is an electron-withdrawing group selected from $CF_3$, halogen-substituted lower alkyl or $(C=O)-O-W_1$, wherein $W_1$ is alkyl, alkenyl, alkynyl, cycloalkyl, cycloalkenyl, cycloalkynyl, aryl, alkaryl, or arylalkyl;
- wherein a fluorophore is covalently linked to one of $R_i$ (i=1-5);
- $R_7$ and $R_{10}$ are independently hydrogen, halogen, lower alkyl, lower alkenyl, halogenated alkyl, CN, or $NO_2$;
- $R_8$, $R_9$, $R_{11}$, and $R_{12}$ are independently hydrogen, halogen, alkyl, halogenated alkyl, alkenyl, keto, aldehyde, carboxylate, carboxylic ester, alkylamino, hydroxyl, alkoxy, alkoxyalkyl, polyether, thiol, alkylthio, cyano, nitro, or of formula —(C=O)—Y or —(C=O)—X—Y, wherein X is a lower alkyl or alkenyl chain, and Y is hydrogen, alkyl, alkenyl, alkynyl, cycloalkyl, cycloalkenyl, cycloalkynyl, aryl, alkaryl, arylalkyl, keto, aldehyde, carboxylate, carboxylic ester, carbamate, amide, amino, alkylamino, hydroxyl, alkoxy, polyether, thiol, alkylthio, cyano, nitro, sulfonyl, inorganic ester, or a 5- to 7-membered heterocyclic ring whose ring atoms are selected from the group consisting of carbon, nitrogen, oxygen and sulfur, wherein the ring atoms include 3 to 6 carbon atoms, and no more than two heteroatoms;

$R_{13}$ is $OR'_4$ or $NR'_5R'_6$, wherein $R'_4$, $R'_5$ and $R'_6$ are independently hydrogen, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether;

$R_{14}$ and $R_{15}$ are independently hydrogen, halogen, alkyl, alkoxy, polyether, or $R_{14}$ and $R_{15}$ come together to form a 5, 6, or 7-membered ring which is aryl, heterocyclic, heteroaryl, or heteroaromatic;

$R_{16}$ is hydrogen, alkyl, alkoxy, or polyether;

$R_{17}$ is an electron-withdrawing group selected from $CF_3$, halogen-substituted lower alkyl or (C=O)—O—$W_2$, wherein $W_2$ is alkyl, alkenyl, alkynyl, cycloalkyl, cycloalkenyl, cycloalkynyl, aryl, alkaryl, or arylalkyl;

$R_{18}$ and $R_{19}$ are independently hydrogen, halogen, alkyl, or alkoxy;

$R_{20}$ is hydrogen, alkyl, alkenyl, alkynyl, cycloalkyl, cycloalkenyl, cycloalkynyl, aryl, alkaryl, arylalkyl, carboxy alkyl, carboxylic ester, or aminoalkyl;

$R_{21}$ and $R_{22}$ are independently hydrogen, alkyl, alkenyl, alkynyl, cycloalkyl, cycloalkenyl, cycloalkynyl, aryl, alkaryl, arylalkyl, keto, carboxy alkyl, carboxylate, carboxylic ester, carbamate, amide, amino, alkylamino, polyether, alkylthio, cyano, nitro, sulfonyl, or inorganic ester; and $R_{23}$ is selected from below:

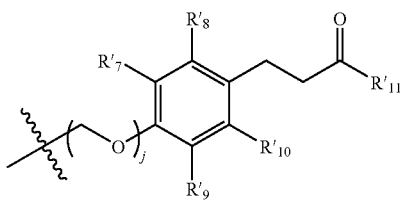

wherein
j=0 or 1;

$R'_7$, $R'_8$, $R'_9$, and $R'_{10}$ are independently hydrogen, halogen, alkyl, alkoxy, alkyloxy, polyether, $R'_7$ and $R'_8$ come together to form a 5, 6, or 7-membered ring which is selected from aryl, heterocyclic, heteroaryl, or heteroaromatic, or $R'_9$ and $R'_{10}$ come together to form a 5, 6, or 7-membered ring which is aryl, heterocyclic, heteroaryl, or heteroaromatic;

$R'_{11}$ is an electronic withdrawing group selected from $CF_3$, halogen-substituted lower alkyl or (C=O)—O—$W_3$, where $W_3$ is alkyl, alkenyl, alkynyl, cycloalkyl, cycloalkenyl, cycloalkynyl, aryl, alkaryl, or arylalkyl; and $R_{24}$, $R_{25}$, $R_{26}$, and $R_{27}$ are independently hydrogen, alkyl, alkenyl, alkynyl, alkoxy, alkyloxy, cycloalkyl, cycloalkenyl, cycloalkynyl, aryl, alkaryl, arylalkyl, keto, aldehyde, carboxylate, carboxylic acid, carboxylic ester, carbamate, amide, amino, alkylamino, polyether, thiol, alkylthio, cyano, nitro, sulfonyl, inorganic ester, $R_{24}$ and $R_{25}$ come together to form a 5, 6, or 7-membered ring which is cycloalkyl, cycloalkenyl, cycloalkynyl, aryl, heterocyclic, heteroaryl, or heteroaromatic, $R_{25}$ and $R_{26}$ come together to form a 5, 6, or 7-membered ring which is cycloalkyl, cycloalkenyl, cycloalkynyl, aryl, heterocyclic, heteroaryl, or heteroaromatic, or $R_{26}$ and $R_{27}$ come together to form a 5, 6, or 7-membered ring which is cycloalkyl, cycloalkenyl, cycloalkynyl, aryl, heterocyclic, heteroaryl, or heteroaromatic.

2. The compound of claim 1, wherein $R'_1$ is $CH_3$.

3. The compound of claim 1, wherein $R'_1$ is $OCH_2OZ_1$.

4. The compound of claim 3, wherein $Z_1$ is alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether.

5. The compound of claim 4, wherein $Z_1$ is $CH_3$.

6. The compound of claim 1, wherein $R_1$ is $NR'_2R'_3$.

7. The compound of claim 6, wherein $R'_2$ is hydrogen.

8. The compound of claim 7, wherein $R'_3$ is (C=O)$Z_2$.

9. The compound of claim 8, wherein $Z_2$ is alkyl, alkenyl, alkynyl, alkoxyalkyl, cycloalkyl, cycloalkenyl, cycloalkynyl, aryl, alkaryl, arylalkyl, or polyether.

10. The compound of claim 1, wherein $R_2$ and $R_3$ come together to form a 5, 6, or 7-membered ring which is aryl, heterocyclic, heteroaryl, or heteroaromatic.

11. The compound of claim 1, wherein $R_4$ and $R_5$ come together to form a 5, 6, or 7-membered ring which is aryl, heterocyclic, heteroaryl, or heteroaromatic.

12. The compound of claim 1, wherein $R_6$ is halogen substituted lower alkyl.

13. The compound of claim 12, wherein $R_6$ is $CF_nH_{3-n}$.

14. The compound of claim 13, wherein n is 1 or 2.

15. The compound of claim 1, wherein $W_1$ is $CH_3$.

16. The compound of claim 1, wherein $W_1$ is tert-butyl.

17. The compound of claim 1, wherein $R_7$ is $CH_3$.

18. The compound of claim 1, wherein the fluorophore is selected from acridine orange, anthracene ring, allophycocyanin, BODIPY, cyanines, coumarin, Edans, Eosin, Erythrosin, fluorescamine, fluorescein, FAM (carboxyfluorescein), HEX (hexachlorofluorescein), JOE (6-carboxy-4',5'-dichloro-2',7'-dimethoxy-fluorescein), Oregon Green, phycocyanin, phycoerythrin, rhodamine, ROX (Carboxy-X-rhodamine), TAMRA (carboxytetramethylrhodamine), TET (tetrachloro-fluorescein), Texas red, tetramethylrhodamine, and xanthines.

19. The compound of claim 1, wherein $R_9$ is (C=O)$NR''_1R''_2$.

20. The compound of claim 19, wherein $R''_1$ is —$(CH_2)_k$—$CH_3$.

21. The compound of claim 20, wherein k is 0-24.

22. The compound of claim 19, wherein $R''_2$ is —$(CH_2)_l$—$CH_3$.

23. The compound of claim 22, wherein l is 0-24.

24. The compound of claim 1, wherein $R_8$ and $R_9$ come together to form a 5, 6, or 7- membered ring, which is cycloalkyl, cycloalkenyl, cycloalkynyl, aryl, heterocyclic, heteroaryl, or heteroaromatic.

25. The compound of claim 1, wherein $R_{12}$ is (C=O)$NR''_3R''_4$.

26. The compound of claim 25, wherein $R''_3$ is —$(CH_2)_p$—$CH_3$.

27. The compound of claim 26, wherein p is 0-24.

28. The compound of claim 25, wherein $R''_4$ is —$(CH_2)_q$—$CH_3$.

29. The compound of claim 28, wherein q is 0-24.

30. The compound of claim 1, wherein $R_{11}$ and $R_{12}$ come together to form a 5, 6, or 7-membered ring which is cycloalkyl, cycloalkenyl, cycloalkynyl, aryl, heterocyclic, heteroaryl, or heteroaromatic.

31. The compound of claim 1, wherein $R'_4$ is $CH_3$.

32. The compound of claim 1, wherein $R'_4$ is $OCH_2OZ_3$.

33. The compound of claim 32, wherein $Z_3$ is alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether.

34. The compound of claim 33, wherein $Z_3$ is $CH_3$.

35. The compound of claim 1, wherein $R_{13}$ is $NR'_5R'_6$.

36. The compound of claim 35, wherein $R'_5$ is hydrogen.

37. The compound of claim 36, wherein $R'_6$ is $(C=O)Z_4$.

38. The compound of claim 37, wherein $Z_4$ is alkyl, alkenyl, alkynyl, alkoxyalkyl, cycloalkyl, cycloalkenyl, cycloalkynyl, aryl, alkaryl, arylalkyl, or polyether.

39. The compound of claim 1, wherein $R_{14}$ and $R_{15}$ come together to form a 5, 6, or 7-membered ring which is aryl, heterocyclic, heteroaryl, or heteroaromatic.

40. The compound of claim 1, wherein $R_{17}$ is halogen substituted lower alkyl.

41. The compound of claim 40, wherein $R_{17}$ is $CF_nH_{3-n}$.

42. The compound of claim 41, wherein n is 1 or 2.

43. The compound of claim 1, wherein $W_2$ is $CH_3$.

44. The compound of claim 1, wherein $W_2$ is tert-butyl.

45. The compound of claim 1, wherein $R_{18}$ is Cl, Br, or I.

46. The compound of claim 1, wherein $R_{18}$ is $CH_3$.

47. The compound of claim 1, wherein $R_{19}$ is Cl, Br, or I.

48. The compound of claim 1, wherein $R_{19}$ is $CH_3$.

49. The compound of claim 1, wherein $R_{20}$ is $-(CH_2)_m-$COOH.

50. The compound of claim 49, wherein m is 1-24.

51. The compound of claim 1, wherein $R'_7$ and $R'_8$ come together to form a 5, 6, or 7-membered ring which is aryl, heterocyclic, heteroaryl, or heteroaromatic.

52. The compound of claim 1, wherein $R'_9$ and $R'_{10}$ come together to form a 5, 6, or 7-membered ring which is aryl, heterocyclic, heteroaryl, or heteroaromatic.

53. The compound of claim 1, wherein $R'_{11}$ is halogen substituted lower alkyl.

54. The compound of claim 40, wherein $R'_{11}$ is $CF_nH_{3-n}$.

55. The compound of claim 41, wherein n is 1 or 2.

56. The compound of claim 1, wherein $W_3$ is $CH_3$.

57. The compound of claim 1, wherein $W_3$ is tert-butyl.

58. The compound of claim 1, wherein $R_{24}$ and $R_{25}$ come together to form a 5, 6, or 7-membered ring which is cycloalkyl, cycloalkenyl, cycloalkynyl, aryl, heterocyclic, heteroaryl, or heteroaromatic.

59. The compound of claim 1, wherein $R_{25}$ and $R_{26}$ come together to form a 5, 6, or 7-membered ring which is cycloalkyl, cycloalkenyl, cycloalkynyl, aryl, heterocyclic, heteroaryl, or heteroaromatic.

60. The compound of claim 1, wherein $R_{26}$ and $R_{27}$ come together to form a 5, 6, or 7-membered ring which is cycloalkyl, cycloalkenyl, cycloalkynyl, aryl, heterocyclic, heteroaryl, or heteroaromatic.

61. An agent for measurement of peroxynitrite, wherein the agent comprises the compound according to claim 1.

* * * * *

UNITED STATES PATENT AND TRADEMARK OFFICE
CERTIFICATE OF CORRECTION

PATENT NO.        : 7,705,040 B2
APPLICATION NO.   : 11/245529
DATED             : April 27, 2010
INVENTOR(S)       : Dan Yang et al.

Page 1 of 1

It is certified that error appears in the above-identified patent and that said Letters Patent is hereby corrected as shown below:

On the Title page item (73),

"The University of Hong Kong" should read -- Versitech Limited --.

Signed and Sealed this
Eleventh Day of January, 2011

David J. Kappos
*Director of the United States Patent and Trademark Office*